US007547526B2

(12) United States Patent
Ladisch et al.

(10) Patent No.: US 7,547,526 B2
(45) Date of Patent: Jun. 16, 2009

(54) CELL CONCENTRATION AND PATHOGEN RECOVERY

(75) Inventors: Michael R. Ladisch, West Lafayette, IN (US); Xingya Liu, West Lafayette, IN (US); Amanda C. Stewart, Kula, HI (US); Wan-Tzu Chen, Lafayette, IN (US); Nathan S. Mosier, West Lafayette, IN (US); Thomas Huang, West Lafayette, IN (US); Jeremiah Bwatwa, West Lafayette, IN (US); Richard Hendrickson, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/081,378

(22) Filed: Mar. 15, 2005

(65) Prior Publication Data

US 2005/0244943 A1 Nov. 3, 2005

Related U.S. Application Data

(60) Provisional application No. 60/553,235, filed on Mar. 15, 2004.

(51) Int. Cl.
*C12Q 1/24* (2006.01)
(52) U.S. Cl. ...................................................... 435/30
(58) Field of Classification Search ........................ None
See application file for complete search history.

(56) References Cited

U.S. PATENT DOCUMENTS

| 5,601,711 | A | * | 2/1997 | Sklar et al. | .................. | 210/238 |
| 5,808,010 | A | | 9/1998 | Ladisch et al. | | |
| 6,716,620 | B2 | | 4/2004 | Bashir et al. | | |
| 2003/0141251 | A1 | * | 7/2003 | Ji et al. | ........................ | 210/653 |

OTHER PUBLICATIONS

Christie, in Advances in Lipid Methodology-Two, pp. 195-213, Ed. Christie, Oily Press, 1993.*
Earlix et al., Dis. Aquat. Org., 27:19-24, 1996.*
Pettipher et al. (Appl. Environ. Microbiol., 44:809-813, 1982).*
Bwatwa et al. (Abstract ANYL-349, Book of Abstracts, 229th ACS National Meeting, Mar. 13, 2005).*
Besse et al. (Food Microbiol., 18:669-676, 2001).*
Cloak et al. (J. Appl. Microbiol., 86:583-590, 1999).*
Ingianni et al. (Mol. Cel. Probes., 15:275-280, 2001).*
Nalgene Catalog 1991, pp. 78-92.*
Ballew et al. (The ABCs of Filtration and Bioprocessing for the Third Millennium, Spectrum Laboratories, Inc., 2002).*
The American Heritage® Dictionary of the English Language Online. Accessed Oct. 15, 2007, http://www.bartleby.com/61/71/A0537100.html.*
The American Heritage® Dictionary of the English Language Online. Accessed Oct. 15, 2007, http://www.bartleby.com/61/73/A0537300.html.*
Morales-Morales et al. (Appl. Environ. Microbiol., 69:4098-4102, 2003).*
Gomez et al. (Biomed. Microdevices, 3:201-209, 2001).*
Morales et al., "Optimization of a Reuseable Hollow-Fiber Ultrafilter for Simultaneous Concentration of Enteric Bacteria, Protozoa, and Viruses from Water", *Applied and Environmental Bicrobiology*, vol. 69, No. 7,.pp. 4098-4102, Biology Dept., New Mexico State Univeristy, Las Cruces, New Mexico, Jul. 2003.
Bhattacharya et al.; "PCR based-detection in a micro-fabricated platform;" Lab Chip; 2008 (submitted).
Liu et al.; "Electrical Characterization of DNA Molecules in solution using impedance measurements;" Appl. Phy. Lett. 92, 143902 (2008).
Rådström et al.; "Pre-PCR Processing: Strategies to Generate PCR-Compatible Samples;" Molecular Biology, vol. 26, 2004; pp. 133-146.
Ramesh et al.; "Application of a convenient DNA extraction method and multiplex PCR for the direct detection of *Staphylococcus aureus* and *Yersinia enterocolitica* in milk samples;" Molecular and Cellular Probes (2002) 16; pp. 307-314.
Rodríguez-Lázaro et al.; "A Novel Real-Time PCR for *Listeria monocytogenes* That Monitors Analytical Performance via an Internal Amplification Control;" Applied and Environmental Microbiology; vol. 71, No. 12; Dec. 2005; pp. 9008-9012.
Wilson; "Inhibition and Facilitation of Nucleic Acid Amplification;" Applied and Environmental Microbiology; vol. 63, No. 10; Oct. 1997; pp. 3741-3751.
Yang et al.; "A multifunctional micro-fluidic system for dielectrophoretic concentration coupled with immuno-capture of low numbers of *Listeria monocytogenes*;" The Royal Society of Chemistry; Lab Chip, 2006, 6, 896-905.
Belter et al. "Downstream Processing for Biotechnology." Wiley-Interscience. pp. 1-9, 15-18, 22-30, 238-239, 242-247. 1988.
Besse et al. "Development of a Membrane Filtration Method for Enumeration of *Listeria monocytogenes* From Soft Cheese." Food Microbiol. 2001. 669-676. vol. 18.
Besse et al. "A Contribution to the Improvement of *Listeria monocytogenes* Enumeration in Cold-Smoked Salmon." International Journal of Food Microbiology, vol. 91, No. 2, Mar. 1, 2004.
Bhunia et al. A Six -Hour In Vitro Virulence Assay for *Listeria monocytogenes* Using Myeloma and Hybridoma Cells from Murine and Human Sources. Microb Pathog. Feb. 1994. pp. 99-110. vol. 16, No. 2.
Bhunia. "Antibodies to *Listeria monocytogenes*." 1997. Crit. Rev. Microbiol. pp. 77-107. vol. 23.
Bobbitt et al. "The Removal of Bacteria from Solutions by Membrane Filtration." Journal of Microbiological Methods, vol. 16, No. 3, 1992, pp. 215-220.
Bwatwa et al. "Rapid Microfiltration of *E. coli*." BIOT Division, Paper 74, 227th ACS National Meeting, Section: Microbial Fermentation Process Development. Anaheim, CA (Mar. 29, 2004).

(Continued)

*Primary Examiner*—Robert B Mondesi
*Assistant Examiner*—Brian J Gangle
(74) *Attorney, Agent, or Firm*—Brinks Hofer Gilson & Lione

(57) ABSTRACT

Methods and kits for the isolation of organisms. Such methods and kits are particularly useful for concentrating and recovering viable organisms from food material. The recovered organisms are of sufficient number and purity to allow detection using a biochip device.

17 Claims, 3 Drawing Sheets

OTHER PUBLICATIONS

Carroll et al. "Development and Evaluation of a 24-Hour Method for the Detection and Quantification of *Listeria monocytogenes* in Meat Products." Journal of Food Protection, vol. 63, No. 3, Mar. 2000, pp. 347-353.

Chen et al. "Rapid Sample Preparation of Foodborne Pathogens by Membrane Filtration." BioMems and Biomedical Nanotechnology, Columbus. Sep. 6, 2002.

Chen et al. "Novel Method for *Listeria monocytogenes* Detection By Bio-Selective Membrane." BMES Annual Meeting, Nashville. Oct. 2003.

Chen et al. "Biofunctional Membrane for *Listeria monocytogens* Detection." Abstract and Presentation Slides. ACS National Meeting. New Orleans. Mar. 25, 2003.

Chen et al. "Mechanistic Study of Membrane Concentration and Recovery of *Listeria monocytogenes*." Biotechnol. Feb. 5, 2005. pp. 263-273. vol. 89, No. 3.

Coulanges et al. "Esculetin Antagonizes Iron-Chelating Agents and Increases the Virulence of *Listeria monocytogenes*". Res Microbiol. 1996. pp. 677-685. vol. 147.

Deisingh et al. "Detection of Infectious and Toxigenic Bacteria." Analyst. 2002. pp. 567-581. vol. 127.

Difco Manual. 1998. pp. 364-366.

Fraser et al. "Rapid Detection of *Listeria* in Food and Environmental Samples by Esculin Hydrolysis." 1988. pp. 762-765. vol. 51.

Gomez et al. "Microscale Electronic Detection of Bacterial Metabolism." Sensors and Actuators. Apr. 23, 2002. pp. 198-208. vol. 86.

Hamaker et al. "Transport Properties of Rolled, Continuous Stationary Phase Columns." Biotechnology Progress. 1998. pp. 21-30. vol. 14, No. 1.

Huang et al. "Composite Surface for Blocking Bacterial Adsorption on Protein Biochips." Biotechnology. 2003b. pp. 618-624. vol. 81.

Huang et al. "Microfiber Assisted Fabrication of Microfluidic Channels Using Polydimethylsiloxane." AIChE Journal. 2003a. pp. 2984-2987. vol. 49.

Hugo et al. Pharmaceutical Microbiology 6$^{th}$ Edition. 1998. p. 23.

Keim et al. Modeling Pore Size Distribution in Cellulose Rolled Stationary Phases. Biotechnology Progress. Mar.-Apr. 2002. pp. 317-321. vol. 18, No. 2.

Ladisch et al. Bioseparations Engineering. 2001. pp. 36-47, 53-113.

Mead et al. "Food-Related Illness and Death in the United States." Emerging Infectious Diseases. 1999. pp. 607-625. vol. 5.

Muhammad-Tahir et al. "A Disposable Biosensor for Pathogen Detection in Fresh Produce Samples." Biosystems Engineering. Mar. 5, 2004. pp. 145-151. vol. 88, No. 2.

Oda et al. "Size Selective Continuous Flow Filtration Method for Detection of Cryptosporidium and Giardia." Water Research. Mar. 1, 2000. pp. 447-4481. vol. 34, No. 18.

Palmgren et al. "The Nucleopore Filter Method: A Technique for Enumeration of Viable and Nonviable Airborne Microorganisms." Am J Ind Med. 1986. pp. 325-327. vol. 10.

Payne et al. "Methods for the Separation and Concentration of Bacteria from Foods." Trends in Food Science and Technology. 1991. pp. 315-319. Food Science 4$^{th}$ Edition. 1986.

Pettipher et al. "Rapid Enumeration of Microorganisms in Foods by the Direct Epifluorescent Filter Technique." Applied and Environmental Microbiology. Oct. 1982. pp. 809-813. vol. 44, No. 4.

Sharpe et al. "Membrane Filtration of Food Suspensions." Applied and Environmental Microbiology. Jan. 1979. pp. 21-35. vol. 34, No. 1.

Sharpe et al. "Stomaching: A New Concept in Bacteriological Sample Preparation." Applied Microbiology. 1972. pp. 175-178. vol. 24, No. 2.

Shaw et al. "Nucleopore Filters as Diffusion Screens: Effect of Barrel-Shaped Pore Distortions." J Aerosol SCi. 1985. pp. 307-313. vol. 16.

Solomon et al. "Transmission of *Escherichia coli* O157:H7 from Contaminated Manure and Irrigation Water to Lettuce Plant Tissue and Its Subsequent Internalization." Applied and Environmental Microbiology. Jan. 2002. pp. 397-400. vol. 68, No. 1.

Soltys et al. "Equilibrium Adsorption of LDL and Gold Immunoconjugates to Affinity Membranes Containing PEG Spacers." Biomaterials. Jan. 2000. pp. 37-48. vol. 21, No. 1.

Stevens et al. "Bacterial Separation and Concentration from Complex Sample Matrices: A Review." Critical Reviews in Microbiology. 2004. pp. 7-24. vol. 30, No. 1.

Suye et al. "Immobilization of Glucose Oxidase on Poly-(L-lysine)-Modified Polycarbonate Membrane." Biotechnol. Appl. Biochem. 1998. pp. 245-248. vol. 27.

Swaminathan et al. "Rapid Detection of Food-Borne Pathogenic Bacteria." Annual Reviews in Microbiology. 1994. pp. 401-426. vol. 48.

Tortorello et al. "Antibody-Direct Epifluorescent Filter Technique for Rapid, Direct Enumeration of *Escherichia coli* O157:H7 in Beef." Applied and Environmental Microbiology. Oct. 1994. pp. 3553-3559. vol. 60, No. 10.

Tortorello et al. "Comparison of Antibody-Direct Epifluorescent Filter Technique with the Most Probable Number Procedure for Rapid Enumeration of *Listeria* in Fresh Vegetables." Journal of AOAC International, vol. 80, No. 6, Nov. 1997, pp. 1208-1214.

USDA/Food Safety Inspection Service (FSIS) Microbiology Laboratory Guidebook, Chapter 3, Section 3.31 "Food Homogenates," 1998.

International Search Report dated Sep. 28, 2005.

* cited by examiner

CELL CONCENTRATION AND PATHOGEN RECOVERY

RELATED APPLICATIONS

This application claims the benefit of the filing date under 35 U.S.C. § 119(e) of Provisional U.S. Patent Application Ser. No. 60/553,235, filed Mar. 15, 2004, which is hereby incorporated by reference in its entirety.

FEDERALLY SPONSORED RESEARCH OR DEVELOPMENT

This invention was made with United States Government support awarded by the Center for Food Safety Engineering, and the United States Department of Agriculture, research grant number USDA 1935-4200-035. The United States Government has certain rights in this invention.

BACKGROUND

Pathogens are causative agents of disease. Food-borne pathogens are pathogens, whether infectious or toxic, that enter the body through the consumption of food. These pathogens which include viruses, bacteria, parasites, toxins, metals, and prions, can lead to illness, hospitalization, or even death in humans (Mead et. al, 1999). The Centers for Disease Control and Prevention have estimated that food-borne diseases cause approximately 76 million illnesses, 325,000 hospitalizations, and 5,000 deaths in the United States each year (Mead et. al, 1999). Mead et al. (1999) have also projected that bacteria cause 72% of the deaths that are attributable to foodborne transmission. Some bacterial species that are of concern are *Salmonella, Campylobacter jejuni, Escherichia coli* O157:H7, *Listeria monocytogenes, Staphylococcus aureus, Clostridium perfringens*, and *Cyclospora cayetanensis*.

Food matrices have complex structures consisting of carbohydrates, proteins, fats, oils, minerals, vitamins, etc., not to mention the different preservatives that are added in order to ensure shelf-life. Consequently, the sampling and analysis of foods for the presence of pathogens offer many challenges. Swaminathan and Feng (1994) noted that these result from the extensive variations in physical characteristics and chemical compositions of foods, the extent of food processing (raw foods to nearly sterile foods packed in hermetically sealed containers), the microorganisms present in foods, and the degree of sublethal injury inflicted on the bacteria present in foods.

Because foods comprise differing organic and inorganic molecules in differing concentrations, pathogens may adjust their metabolism accordingly for survival. This response is not beneficial if the goal is to rapidly detect pathogens because there may be some surface antigen or modification that may or may not be expressed so a preenrichment step is often performed in order to resuscitate the injured or stressed bacteria to resume its normal metabolism. A preenrichment step not only salves bacteria but can also serve to increase the number of pathogenic microorganisms that may be outnumbered from the indigenous microflora in a matrix (Swaminathan and Feng, 1994, Stevens and Jaykus, 2004).

The use of culture enrichment and selective plating are good, quality, conventional tools to identify specific pathogens, but they are very lengthy and may take up to four days to obtain even preliminary results (Stevens and Jaykus, 2004). While a confirmation of whether a food sample is pathogen-free is being waited for, a consumer may have already consumed it. Therefore, there needs to be some way of rapidly separating and concentrating pathogens from a food matrix for their detection.

Separation and concentration are important because they offer advantages of facilitating the detection of multiple bacterial strains, removal of matrix-associated reaction inhibitors, and providing ample sample size reductions to allow for the use of smaller media volumes (Stevens and Jaykus, 2004). A battery of tests exists that may be used for the detection of bacteria. A direct epifluoresent filter technique (DEFT), which combines enumeration and microscopy, has been used to detect bacteria (Hugo and Russell, 1998). This technique concentrates bacteria from a large sample volume using a polycarbonate filter. The bacteria are then stained with acridine orange for enumeration (Deisingh and Thompson, 2002). Bioluminescence for adenosine triphosphate (ATP) has been used in the analysis of fresh meats and other foods for microorganisms (Swaminathan and Feng, 1994). Immunological approaches have been used for the detection of bacteria which use enzyme-linked immunosorbent assay (ELISA) and immunomagnetic separation (Deisingh and Thompson, 2002).

These methods usually cannot be used directly with foods due to the presence of interfering materials and to the low numbers to target cells (Payne and Kroll, 1991). Particularly, when using microfluidic-based sensors, samples have to be almost particulate or colloidal free for successful pathogen detection. When particulates are present, they may alter the metabolism of pathogens and/or cause a false positive or negative result. Thus, there is a need in the art for sequestering pathogens from food matrices in a way that provides a detectable amount of bacteria in a relatively particulate- or colloidal-free sample.

The background information above is provided to set forth the nature of some of the problems addressed by the present invention. Inclusion of a reference or work by others in this section is not an admission that such work or reference is prior art to the present invention.

BRIEF SUMMARY

This application provides methods, devices, and kits that satisfy the need in the art for sequestering organisms, such as pathogens, from food in a way that provides a sufficient amount of bacteria for detection in a relatively particulate- or colloidal-free sample. The methods allow for rapid concentration and detection of viable organisms in a sample, such as a food sample. In addition, the methods allow rapid concentration and detection of organisms from large volumes of organism-containing liquids. The relatively particulate- or colloidal-free sample can be placed on a biochip for interrogation/detection.

The rapid concentration and recovery of organisms, such as microbes, for the purpose of interrogation on a biochip may require a sequence of membrane separation and filtration steps, carried out in the presence of optimized buffers with a system of membranes optimized for such a task. Multiple steps and optimization are often needed because, when food samples are being probed for pathogens, they are homogenized or otherwise finely divided in order to separate the organisms from the food material. Because lipids, fat particles, aggregated proteins, cellular material, and tissue particulates are present in the sample, such components should be separated from the liquid containing the organisms in a rapid and complete manner.

The methods described provide a sequence of events that include 1) homogenization or blending of food material; 2)

the initial separation of liquid from solids while avoiding loss of the organisms with the food particles and while maintaining the viability of the organisms; 3) concentration of organisms in a large volume of liquid, e.g., 200 ml, to very minute volumes, e.g., 10 μl; and 4) recovery of cells in a liquid suspension that is suitable for introduction into a biochip. Because often the assay is used to detect as little as 1000 cells per liter, large volumes of the sample must be processed rapidly. Consequently, in certain examples, 200 ml of liquid is concentrated down to 10 μl in less than 30 minutes. The fluid at the end of such processes contains viable cells that can be probed for the presence of organisms, such as pathogens.

The methods disclosed here are often multi-step processes. The processes tend to be more complex when the makeup of the starting material is complex. If water or some other solid-free fluid is to be tested, only one or two steps are typically needed. When the starting material is vegetable matter, meats, or other complex food materials, up to 5 steps may be needed, e.g., homogenization or stomaching the sample in a suitable buffer; prefiltering, centrifugation or other pre-processing steps; membrane filtration; microfiltration (2 or 3 micron cut-off); and final filtration and cell recovery (e.g., using a sheet or hollow fiber having 0.5 micron or less cut-off) in a buffer suitable for delivery to a biochip. The sequence of steps, buffers, and other conditions described provide successful recovery of viable cells in a concentrated state suitable for introduction into a biochip.

A method of isolating an organism from food material is provided. The method comprises processing the food material to create an organism-containing liquid component; separating non-liquid material from the organism-containing liquid component; contacting a cell recovery membrane with the organism-containing liquid component, and removing the organism from the cell recovery membrane. The volume of the organism-containing liquid component may be reduced to increase the concentration of organisms therein. Such reduction of volume may be obtained using tangential flow filtration with a hollow-fiber filter.

Kits for performing the methods are also disclosed. A kit may include a preparation buffer, a pre-filter, a cell recovery membrane, and a cell recovery buffer. The kit may further include a syringe, pump, holder for the pre-filter or recovery membrane, a rolled stationary phase, a hollow-fiber filter, or a recovery container. The holder for the pre-filter and the holder for the recovery membrane can be connectable to allow filtration and recovery in series.

DETAILED DESCRIPTION OF THE PRESENTLY PREFERRED EMBODIMENTS

Figure 1:
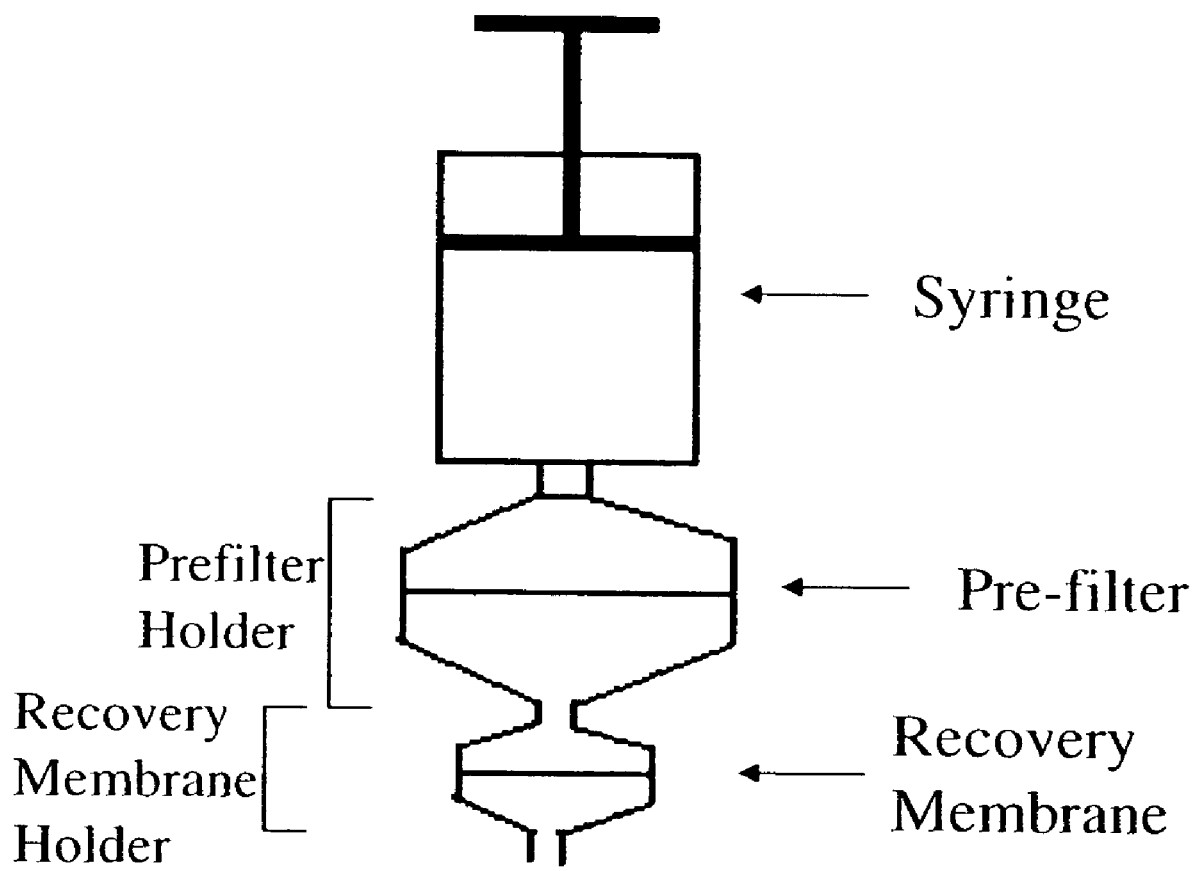
FIG. 1 is a schematic of preferred kit component arrangement. Not included in the schematic is a collar connecting the pre-filter holder and the recovery membrane holder.

Methods for isolating particles from a sample are provided. In certain examples, "isolating" refers to the strict standard of separating one or more of the particles into a pure population. In other examples, "isolating" occurs when one or more of the particles are substantially separated from other components of the sample but not to the extent that it is a pure population of that particle, e.g., one or more different types of organisms may be together in the product of the isolation. When the particle is an organism, the isolated organism may be viable or non-viable. Preferably, the isolated organism is a viable organism in concentrated form.

Examples of particles that may be isolated include, organisms, spores, and nano-particles. Organisms that may be isolated include bacteria, viruses, fungi, and protozoans. Bacteria may be gram-positive, such as *Streptococcus* spp., *Staphylococcus* spp., *Clostridium* spp., and *Listeria* spp., such as *L. monocytogenes* and *L. innocua*, or gram-negative, such as *Salmonella* spp, *Shigella* spp. *Vibrio cholorae*, and *E. coli*. The organism may be wild-type, mutant, or genetically-engineered. Viruses that may be isolated include bacteriophage, non-enveloped viruses, such as picornavirus and rhabdovirus, and enveloped viruses, such as aophavirus, retrovirus, paramyxovirus, orthomyxovirus, and pox virus. Fungi that may be isolated include *Saccharomyces* spp., *Acremonium* spp., *Aspergillus flavus, Fusarium* sp., and *Paecilomyces lilacinus*.

The sample may be virtually any material suspected of containing an organism of interest. Exemplary samples include liquid samples, such as fruit and vegetable juices, bottled water, airplane water, process water, waste water, and wash liquids from foods or food processing equipment. The sample may also be a medical sample, such as blood, plasma, urine, feces, or tissue biopsy. Other samples include foods, such as meats, fruits, vegetables, fermented beverages, and dairy products.

Certain samples are simple in makeup. An example of a sample with a simple makeup is a water sample. Typically, for simple samples, isolating an organism from the sample is relatively straightforward. For complex samples, such as foods, tissue samples, or other biologically-derived materials, however, it may be necessary to perform several processing steps to allow adequate recovery of isolated organisms. This is particularly true in instances when the isolated organism is to be detected with equipment that is sensitive to impurities, such as a biochip.

Preferably, though not necessarily, the sample is processed to create an organism-containing liquid component and this liquid component is then separated from non-liquid material. Processing steps can include dilution, blending, chopping, centrifugation, filtrations such as vacuum filtration through various depth filters and filter aid facilitated filtration, processing through rolled stationary phase (preparation of the phase is described by Keim et al. 2002), enzyme treatment (e.g., lipases, proteases, amylases), lipid extraction (e.g., with ethanol, methanol, and/or hexane), massaging, and contacting the solution with positively-charged or negatively-charged membrane materials or particles. A single processing step may be used one or more times or two or more processing steps may be used in combination. In light of the present description, one of skill in the art would understand how to test the various processing steps and combinations of processing steps to optimize recovery of organisms from a particular sample.

In certain applications, samples are diluted in a solution, such as water or a buffer. Preferred solutions are those that maintain the viability of the organism, such as phosphate buffered saline or sodium citrate buffers. The pH of the solution may be optimized to the particular organism to be recovered from the food material.

The solution may contain one or more components that facilitate the recovery of an organism from the food material. For example, solution may be a buffer containing a detergent, such as the nonionic surfactants TWEEN-20 (polyoxyethylene sorbitan monolaureate), TRITON X-100 (octyl phenol ethoxylate), and polyethylene glycol or an ionic detergent, such as sodium dodecyl sulfate (SDS). Preferred concentration ranges of detergent in the buffer include those that facilitate the recovery of an organism from the food material but maintain the viability of the organism, such as between 0.001%, 0.01%, 0.1%, 0.2%, 0.3%, 0.4%, or 0.5% and 0.6%, 0.7%, 0.8%, 0.9%, 1.0%, 1.1%, 1.2%, 1.3%, 1.4%, 1.5%, or 2.0%.

As described in the Examples, 1% TWEEN 20, a non-ionic detergent used to eliminate non-specific binding for immunoassays, significantly enhanced *L. monocytogenes* recovery by a factor of between 5 to 20 when the initial solution had counts of 700 cells (as cfu)/mL in massaged hotdog broth. After filtration, a viable cell recovery rate of as much as 86% was obtained.

The dilution may occur prior to, during, or after processing the sample material. Food material samples may be diluted for optimization of organism recovery from a given type of food sample. Parameters to consider when diluting the food material samples include, but are not limited to, the composition of the food material, the quantity of food material that would be needed to yield a sufficient number of organisms, and the possibility of the solution plugging the membranes and filters used to recover organisms. Dilution ratios include dilutions of at least 1:1, at least 1:2, at least 1:3, at least 1:4, at least 1:5, at least 1:6, at least 1:7, at least 1:8, at least 1:9, at least 1:10, at least 1:15, at least 1:20, at least 1:25, at least 1:30, at least 1:40, at least 1:50, at least 1:75, and at least 1:100.

Dilutions may be made that create a large volume of organism-containing liquid to be further processed. Volumes of 5 ml or more, 10 ml or more, 15 ml or more, 20 ml or more, 25 ml or more, 30 ml or more, 35 ml or more, 40 ml or more, 50 ml or more, 75 ml or more, 100 ml or more, 150 ml or more, 200 ml or more, 250 ml or more, 300 ml or more, 400 ml or more, 500 ml or more, 750 ml or more, 1000 ml or more, 1500 ml or more, and 2000 ml or more are specifically contemplated.

When processing large volumes of liquid, a pump, such as a peristaltic pump, may be used. For example, the Rainin Dynamax RP-1 peristaltic pump is able to maintain speed stability at back pressures up to 72 psi, which exceeds the back pressure limits of a syringe pump. A preferred tubing used with the pump is Silicone 2.8 mm tubing with bonded collars. Silicone tubing is preferred because this material is known to be biocompatible.

When making large dilutions, the amount of time required to process a given volume of fluid should be considered. Thus, it may be desirable to limit the amount of dilution to prevent the need to handle large volumes of organism-containing liquids. Thus, dilution ratios also include those of less than 1:50, less than 1:100, less than 1:75, less than 1:50, less than 1:40, less than 1:30, less than 1:25, less than 1:20, less than 1:15, less than 1:10, less than 1:9, less than 1:8, less than 1:7, less than 1:6, less than 1:5, less than 1:4, less than 1:3, and less than 1:2. Of course, ranges of dilutions above are specifically contemplated. For example, a preferred dilution range may be at 1:2 to 1:100, 1:5 to 1:50, and so forth. Preferably, though not necessarily, the food material is diluted about 1:10 prior to processing the food material.

Another processing step is blending. The sample may be processed using a Seward STOMACHER lab blender (Thetford, Norfolk, UK) (referred to herein as "Stomaching"). The STOMACHER lab blender has two paddles and a baffle which serve to shape the food into a ring and use a combination of stirring and crushing to homogenize the food. This technique has been shown to release more deep-seated microbes than other food safety sample preparation methods (Sharpe et at. 1972). This method is of practical application to food pathogen research because it provides a way of disrupting bacterial interactions on and in food surfaces while allowing cells to remain viable. Use of a STOMACHER lab blender is listed as a standard method in the USDA/Food Safety Inspection Service (FSIS) Microbiology Laboratory Guidebook, Chapter 3, section 3.31 "food homogenates."

In one embodiment, 50 g of food sample (i.e., hot dog, vegetable, etc) is added into a sterile plastic bag together with 250 mL of PBS buffer (pH 7.4) giving a 1:6 dilution. The plastic bag is then sealed and put into a STOMACHER 4000 Circulator machine. The machine operates at a RPM of 230 for a duration of 2 minutes at room temperature.

Alternatively, the sample is processed using a blender containing blades, such as a kitchen blender, for shearing the material in the sample. 50 g of food sample (i.e., hot dog, vegetable, etc) is added into a blender jar together with 250 mL of PBS buffer (pH 7.4) giving a 1:6 dilution. The food sample is sheared with blades for 2 minutes at room temperature. The chopped homogenized food sample is then poured into a plastic bag.

After producing an organism-containing liquid component, it may be necessary to separate non-liquid material in the processed sample from this liquid component. Methods of separation include centrifugation and filtration. Examples of useful filters include depth filters and straight pore filters composed of cellulose, nitrocellulose, DEAE-cellulose, polycarbonate, or nylon. Other useful filters include those made of mixed cellulose ester, polyvinylidene fluoride, glass fiber, and ceramics. In instances where the filter comprises pores, preferred average pore diameters are those of greater than 1 micron, greater than two microns, greater than 3 microns, greater than 4 microns, greater than 5 microns, greater than 6 microns, greater than 7 microns, greater than 8 microns, or greater than 9 microns and less than 50 microns, less than 40 microns, less than 30 microns, less than 25 microns, less than 20 microns, less than 15 microns, less than 14 microns, less than 13 microns, less than 12 microns, and less than 11 microns. More preferred average pore diameters are those between 2 an 20 microns.

A filter aid, such as diatomaceous earth, is added to the solution prior to filtration. The two types of filter aids which are most effective for fermentation-derived bioproducts are diatomaceous earths and perlites. Diatomaceous earths are skeletal remains of tiny aquatic plants. Perlites are volcanic rocks processed into a coarse powder. They have a pH range from 7.0 to 10 and can enhance the flowrate by a factor of 200 to 7500× over filtrations where the filter aids are not used (Belter, et al., 1988). The amount of filter aid added can be optimized for the particular sample type. As with the other steps, when attempting to isolate viable organisms, care should be taken that the filter aid does not kill the organism during the isolation process.

In some applications, an organism is isolated from a complex food sample that contains, particles, fats, protein matter, along with the organism. A method of separating the organism from the other materials includes rolled stationary phase (RSP) filtration. This approach uses a textile fabric as described in U.S. Pat. No. 5,808,010, which is incorporated by reference in its entirety. The rolled stationary phase in the '010 was used for chromatography, while for the present application, it is used for filtration. Examples of recovery rates of viable organisms from RSP filtration include 40-50%.

The fabric, if packed in a "tight" manner, retains the advantage of lower pressure drop of a fiber based stationary phase, and in addition gives the sorbent a diameter characteristic which is analogous to a monodisperse particulate stationary phase, but at a fraction of the cost of existing stationary phases. Since the diameter of the yarn and the density of the fabric are almost the same in any place of the fabric, the geometry of the stationary phase is also similar in any place of the column, i.e., uniform packing is assured. The fibers in the yarns are closely related with each other in both warp and filling directions, and give mechanical support of the fabric when packed into the column. A fabric stationary phase is therefore resistant to compaction at high pressure and flow rate. Derivitization of the fabric is readily carried out, and can be easily done on a large scale using existing, and cost effective manufacturing techniques associated with dyeing, crosslinking, or finishing of textile yarns and fabrics.

After separating non-liquid material from the organism-containing liquid component, a cell recovery membrane can be contacted with the liquid component. Preferably, the cell recovery membrane reversibly binds the organism in the liquid component. In certain applications, the cell recovery membrane is a microfiltration membrane comprising pores having a diameter of 0.5 μm or less, 0.45 μm or less, 0.4 μm or less, 0.35 μm or less, 0.3 μm or less, 0.25 μm or less, or 0.2 μm or less. In other applications, the cell recovery membranes is a microfiltration membrane comprising pores having an average diameter of 0.5 μm or less, 0.45 μm or less, 0.4 μm or less, 0.35 μm or less, 0.3 μm or less, 0.25 μm or less, or 0.2 μm or less. Preferred microfiltration membrane materials include polycarbonate and also mixed cellulose, ion exchange cellulose, and nylon. Of course, the optimal pore size and membrane composition material may vary with the size, hydrophobicity, and charge of the organism.

The microfiltration membrane may be treated so to block nonspecific binding of the organism, e.g., pre-treatment of the membrane with a buffer comprising a surfactant or protein additive, such as BSA. Concentrations of surfactant in the buffer useful for this pre-treatment include those between 0.001% and 1% by volume but higher concentrations, such as 1.5% or 2.0%, may be used as long as the membrane of the organism is not compromised or when recovery of viable organisms is not intended. Of course surfactant concentrations can in the above range and greater than or less than 0.01%, greater than or less than 0.1%, and greater than or less than 0.5%. A preferred surfactant is TWEEN-20 (polyoxyethylene sorbitan monolaureate).

In certain applications, the cell recovery membrane comprises a protein that selectively binds the organism. It is contemplated that the protein that selectively binds the organism is attached to the cell recovery membrane by a linker, such as polylysine. Preferably, though not necessarily, the protein is an antibody. Antibodies that selectively bind certain organisms are well known in the art. Typically, the antibody recognizes a protein or other structure on the surface of the organism. Such protein or other structure is often unique to that organism, its species, or its genus. Methods of binding antibodies to materials are well known in the immunoassay art. As with many immunoassays, it is preferred to block non-specific binding by the addition of a protein that does not selectively bind the organism, such as bovine serum albumin (BSA).

Typically, to isolate the organism, it must be removed from the cell recovery membrane. Methods of removing the organism include back flushing or by force such as vortex mixing in the presence of a liquid, such as a recovery buffer. The recovery buffer can contain an effective amount of a surfactant. Preferred concentrations of surfactant in the recovery buffer are those between 0.01% and 1% by volume but higher concentrations, such as 1.5% or 2.0%, may be used as long as the membrane of the organism is not compromised or when recovery of viable organisms is not intended. Of course surfactant concentrations can in the above range and greater than or less than 0.05%, greater than or less than 0.1%, and greater than or less than 0.5%. One surfactant that may be used is TWEEN-20 (polyoxyethylene sorbitan monolaureate).

Preferably, though not necessarily, a minimal amount of recovery buffer is used. When sufficiently small volumes of recovery buffer are used, the methods described herein may create a concentration in the recovery buffer of at least 10× greater, at least 20× greater, at least 50× greater, at least 100× greater, at least 500× greater, at least 1000× greater, or at least 1500× greater than the concentration of organisms in the organism-containing liquid component.

Once isolated the organism may be detected using standard procedures. Examples include plating on selective or indicator media, PCR, real-time PCR, immunoassays, fiber optic probes, flow cytometry, press fit microdevices, and biochips. Biochips are microfabricated devices capable of measuring changes in impedance of small amounts of fluid, thereby providing a method for detecting living microorganisms whose activities secretes components whose presence may change impedance.

Gomez et al. (2002), incorporated herein by reference in its entirety, describes microscale electronic detection of bacterial metabolism. The reference describes a microfluidic biochip that measures changes in impedance of two electrodes in contact with a liquid where the bacteria are cultured. The change in impedance is caused by the release of ionic species by the metabolizing cells. Thus, the presence of viable versus non-viable cells can be determined using the described biochip. Viability determination is important because certain food preparation processes may kill organisms present in the food. In many cases, the presence of dead organisms may not be of concern because such organisms cannot cause disease.

Because the methods described herein are capable of creating extremely pure samples of concentrated organisms in a small volume, one may detect the organism using a biosensor or biochip. An exemplary biosensor is disclosed in U.S. Pat. No. 6,716,620, which is incorporated by reference in its entirety. As disclosed in that patent, apart from small fluid volumes it is preferred that the organism is within a low-conductivity buffer, i.e., those having a sufficiently low concentration of charge carriers to enable detection of a difference in an impedance parameter, such as magnitude or phase, between a bacteria-containing sample and a reference sample free of bacteria.

As described above, methods known in the art for detecting a viable organism in a sample, particularly a food sample, often require culturing of the organism for several days. Using the methods described herein, detection of an organism in food material can be done in less than eight hours, less than four hours, less than two hours, less than one hour, and often less than one half hour.

In alternative methods for isolating an organism from a sample, rather than binding the organism to a recovery membrane, the volume of the organism-containing liquid component is reduced thereby increasing the concentration of organisms therein. This volume reduction can be obtained using hollow fiber filtration. Preferred hollow fiber filters are those comprising fibers having an average pore diameter of less than 0.5 μm and that have been treated with BSA blocking solution (2 mg/ml BSA dissolved in PBS) overnight at 4° C.

Kits

Included within the scope of the invention are kits for isolating an organism, particularly a viable organism, form a sample. Components of the kit may include one or more of the group consisting of a syringe, a syringe pump, a peristaltic pump, a preparation buffer, a pre-filter, a holder for the pre-filter, a rolled stationary phase filter, a holder for the rolled stationary phase filter, a cell recovery membrane, a holder for the cell recovery membrane, a hollow fiber filter, a recovery buffer, and a recovery buffer. One of the components of the kit may be a manual or CD for instructional use.

The preparation buffer preferably contains a surfactant, such as TWEEN-20, at a concentration of between 0.001% and 1%. The recovery buffer similarly contains a surfactant, such as TWEEN-20, but at a concentration of between 0.01% and 1%. As is apparent from the overlapping ranges of TWEEN-20 in the preparation and the recovery buffer, a kit may contain a buffer that serves as both the preparation and the recovery buffer.

The pre-filter preferably has an average pore diameter of between 2 and 20 μm. The cell recovery membrane can be a microfiltration membrane comprising pores having an average diameter of less than 0.5 μm, 0.4 μm, 0.3 μm, or 0.2 μm. The microfiltration membrane is preferable polycarbonate or mixed cellulose. The cell recovery membrane may comprise a protein or compound that selectively binds a particular organism as described above. Alternatively, the kit may contain components for producing such a cell recovery membrane, such as an antibody, a linker, and BSA.

When a hollow fiber filter is included in the kit. It is preferred that the average pore size is 0.5 μm or less, 0.45 μm or less, 0.4 μm or less, 0.35 μm or less, 0.3 μm or less, 0.25 μm or less, or 0.2 μm or less. Various configurations of hollow fiber modules can be included such as 1-fiber, 3-fiber, and 6-fiber configurations. Preferred hollow fibers are polysulfone having an average pore size of either 0.2 or 0.45 μm and an outer diameter of 360 μm with an inner diameter or 280 μm. The preferred length of fiber is 10 inches, although lengths as short as 1 cm may be used. Furthermore, multiple hollow fibers may be bundled As shown in FIG. 1, a syringe 10 is connectable to the pre-filter holder 20, which in turn is connectable to the cell recovery membrane holder 30. In this configuration, the processed sample is placed in the syringe and upon pressure on the syringe plunger the processed sample contacts the pre-filter. The organism-containing liquid component of the processed sample then comes in contact with the cell recovery membrane, which reversibly binds the organism letting the liquid component flow through.

A preferred kit protocol is as follows:

A Pre-filter is centered of a 47 mm holder and then a Cell Recovery Membrane is centered on a 25 mm holder. O-rings on top of the membranes are located and the holders sealed. The two filter holders are then connected to form a membrane couple (FIG. 1). Draw 4 ml of Preparation Buffer into a 3 mL syringe, connect syringe to membrane couple and push Preparation buffer through the membranes. Make sure all the Preparation Buffer has passed through the membranes before the samples are run. Pull 100 mL organism-containing liquid into a 140 ml syringe. Connect syringe containing 100 mL sample to membrane couple (holders) (FIG. 1). Position the syringe-membrane couple system in syringe pump (PHD 4400) and set the infuse rate at 5-10 mL/min. Mount and keep the syringe system and pump at ready (vertical) position. It takes approximately 20 minutes to finish the filtration. Filtration is complete when no droplet is coming out from the 25 mm holder.

Remove membrane couple by twisting the larger device counter-clockwise. Cover the bottom with the cap from a 3 ml syringe and add 1 ml of Recovery Buffer to 25 mm holder through the passway on top of it. Cover the top with lid. Vortex the holder for 3 minutes. Remove lid and withdraw the liquid from the 25 mm holder with the 3 mL syringe. Inject liquid in microcentrifuge tubes.

For a biochip sample, put liquid in 250 μL Microcentrifuge Tube drop by drop. Multiple tubes will be needed depending on how much volume is left after withdrawing from holder. Then place 250 μl tube into a 1.5 mL Microcentrifuge Tube. Centrifuge at 11000 rpm for 3 minutes. Open tube and remove the supernatant with a tip designed to leave 10 μL in the tube for interrogation using a biochip device.

EXAMPLES

Example 1

This example describes optimization of membrane and buffer conditions for the recovery of *Listeria monocytogenes*. The results described herein were published in Chen et al., February 2005. Detection of the foodborne pathogen *Listeria monocytogenes* requires that food samples be processed to remove proteins and lipids, concentrate microorganisms to a detectable concentration, and recover the concentrated cells in a small volume compatible with micron-scale biochips. Mechanistic considerations addressed in this example include the roles of membrane structure, pore size, and detergents in maximizing recovery of cells from a complex biological fluid. The fluid in this case was a food sample (hotdog extract) inoculated with *L. monocytogenes*.

Materials and Methods

Preparation of Hotdog Meat (HDM) Broth

To produce the hotdog extract, a volume of 250 ml of phosphate buffered saline (PBS, pH=7.4) buffer was mixed with each package of hotdogs containing 250 g of meat. The PBS consisted of 8 g NaCl in 10 mM phosphate buffer. The buffer was gently contacted with the hotdogs in a STOMACHER bag that consisted of 2 chambers. The hotdogs were held in an inner chamber and massaged at 10 min intervals for 2 hours while immersed in PBS. The sieve inside the STOMACHER bag separated large food particles from a turbid fluid containing proteins, lipids, carbohydrates, and microbes. The hotdog solution was then decanted from the bag into a filtration unit and filtered across a 0.22 □m cellulose membrane (Nalgene, Cat #121-0020) to remove food particles and microbes so that controlled experiments with *L. monocytogenes* could be carried out. The filtrate (i.e., HDM broth) gave no colony forming units, showing that the initial HDM is free of microorganisms.

Culture of *L. monocytogenes* in HDM Broth and Determination of Colony Forming Units Freshly cultured *L. monocytogenes* in BHI was inoculated into sterile filtered HDM broth. Serial dilution with HDM broth was carried out to a final concentration of 50-70 CFU/100 μL. Colony counts were determined by plating out 100 μL of the diluted HDM broth on MOX agar (selective media for *Listeria* spp.) using a spreader. The plates (3 inch in diameter) were incubated at 37° C. and the number of colonies counted after 24 hours, with each colony apparently formed from a single microbial cell. A volume of 100 mL HDM broth (pH 7.4) was inoculated with *L. monocytogenes* in the concentration of 400 cells/μl and incubated at a shaker rpm of 150 for 12 hours. Samples were taken every hour, appropriately diluted, and 100 μl was plated on MOX agar. A lag phase of about two hours was noted during which the bacteria adjusted to the new environment. A typical log phase growth was observed after 6 hours. On this basis, the filtration testing was carried out within two hours, where the bacteria number remained approximately constant.

FITC Labeling of *Listeria monocytogenes*

Labeling of *L. monocytogenes* was carried out by using fluorescein isothiocyanate (FITC, Sigma, Cat # F4274). 2 mg of FITC was dissolved in 1 ml of bicarbonate buffer (pH 9.6). One milliliter of freshly cultured bacteria was centrifuged at 10000 rpm for 5 minutes. FITC was added to the precipitate and subsequent mixing and incubation of bacteria were carried out for 40 minutes. The cells were then rinsed with bicarbonate buffer three times (Bhunia et al., 1994). This was followed by serial dilution in HDM broth.

Membrane Filtration Procedure

Polypropylene syringe filter holders (13 mm, Fisher Scientific, Cat #5X0001300) sealed with a silicone gasket were used to hold the membranes. Preliminary tests were carried out in the absence of TWEEN-20. The membranes were wetted in PBS buffer (pH 7.4) and different volumes of inoculated HDM broth were manually forced through the membranes at room temperature by applying pressure on the syringe plunger. The membranes were then removed and soaked in 500 μL PBS in 1.5 ml microcentrifuge tubes for 30 minutes with gentle shaking (Eppendorf, Cat #05402-24c, polypropylene). An aliquot of the resulting solution (100 μL) was plated out in triplicate on modified Oxford agar (MOX) and incubated for 48 hours at 37° C. Filtrates were also sampled and plated out on MOX agar to check for presence of bacteria but no significant number was found.

Membranes

*L. monocytogenes* adsorbs on hydrophobic surfaces (Huang et al., 2003). Thus, membranes with hydrophilic surfaces were selected to minimize adsorption and maximize recovery of microorganisms. However, hydrophilic character alone, was found to be insufficient to ensure 95% recovery of the microorganisms. Since the organism of interest, *L. monocytogenes*, has dimensions of 0.5×1.0 micron and does not aggregate at the pH of the buffer (pH 7.4), the membrane cut-off needed to be smaller than this. Hence, 0.2 to 0.45 micron pore size cut-offs were selected.

The membranes tested in this study were made of nylon (Magna Nylon, 0.45 μm, Cat #R045P01300, Batch #163519, Osmonics), mixed cellulose esters (MicronSep, 0.45 and 0.22 μm, Cat #E04WP01300, Lot #78317, Osmonics), polyvinylidene fluoride (PVDF, 0.45 μm, Cat #HVHP01300, Lot #RIHN96852, Millipore) and polycarbonate (Nucleopore 0.4 and 0.2 μm, Cat #0930053, Lot #2134023, Whatman). The membranes were gently dipped in either PBS buffer (pH7.4) or PBS-1% v/v TWEEN-20 (PBST) in order to pre-wet them before testing.

PVDF and nylon membranes are hydrophilic and chemically robust, while mixed cellulose membranes consist of mixed cellulose esters (cellulose nitrate and cellulose acetate). The pores in these membrane matrices are characterized by a tortuous path rather than straight through pores. The Nucleopore polycarbonate membrane is made by track-etching techniques giving straight through pores with defined and relatively uniform radii (Ladisch, 2001). Pores on Nucleopore polycarbonate membrane filter have defined path and sizes, which made it useful in aerosol filtration (Palmgren et al., 1986; Shaw, 1985). Depth membrane filters (nylon, mixed cellulose and PVDF), on the other hand, have tortuous structures, which make them good candidates for removing unwanted substances, but less attractive for cases where the solids are to be recovered from the filter since these are entrapped in the filter.

Membrane Imprint Assay

A membrane imprint assay was used as a rapid way to screen the concentration of *L. monocytogenes* by different membranes. Moreover, the ability of *L. monocytogenes* to hydrolyze the esculin on MOX agar can help differentiate *L. monocytogenes* from other bacteria that are incapable of hydrolyzing esculin.

After the filtration step was carried out, the membranes were removed from the filter holder and then directly placed on MOX agar, retentate side down, and incubated at 37° C. for 48 hours. The agar contained esculin and ferric ammonium citrate to give blackening of the colonies while lithium chloride offered selectivity for *L. monocytogenes* because this microorganism has high tolerance of salt (Fraser and Sperber, 1988). The nutrients in the agar diffused into the membranes and dark-colored colonies of bacterium, if present, developed on the membrane surface after 24 hours. This gave a first indication of whether *L. monocytogenes* had been retained by the membrane.

Studies have shown that lack of iron ions will decrease the growth and reduce the virulence of *L. monocytogenes* (Coulanges et al., 1996). The membrane imprint assay on MOX agar not only screens different membrane filters, but is selective for *Listeria* species over *E. coli* (Difco Laboratories, 1998). However, it is crucial to maintain the MOX agar at 37° C. where lower numbers of *L. monocytogenes* colonies can be fully developed (Fraser and Sperber, 1988).

Bradford Protein Assay

Filtrates were examined for protein concentration using the Bradford protein assay (Catalog No. #500-0006, Bio-Rad). One part of the staining solution was mixed with four parts of deionized water. A volume of 100 μL sample was added to 5 ml of the pre-mixed staining solution. The mixture was gently shaken and incubated for 5 minutes at room temperature. Its absorbance at 595 nm was read with a spectrophotometer. Proteins passed through both the polycarbonate (etched pores) and cellulose (tortuous pores) membranes as indicated by protein analysis that showed both initial solution and permeate were the same at 0.12±0.002 mg/mL.

Scanning Electron Microscopy (SEM)

SEM of membrane filters and *L. monocytogenes* solutions on membrane surfaces were taken after the samples were fixed to the membrane with 2% of glutaraldehyde in PBS. Subsequent washing was carried out and followed by dehydration with increasing concentrations of ethanol. Samples then were dried in critical point drying (CPD) where ethanol is replaced with liquid $CO_2$. Temperature and the pressure were then changed to 34° C. and 1100 psi, respectively, where $CO_2$ vaporized so that the samples were dried. Each membrane sample was mounted to a stud and sputter-coated with AuPd. The images were obtained under 5 kV, with working distance (WD) of 10 mm or 22 mm in vacuum chamber. The magnification was 7000.

Results

Initial assessment of membrane performance for cell concentration was based on a 48 hour membrane imprint assay in order to quickly screen membrane candidates. This was followed by the more labor-intensive but quantitative culture methods that assessed not only microbial retention by the membrane but also the extent of recovery of viable microorganisms. When complete retention but low recovery of the microorganisms was encountered, the potential role of membrane structure on microbial entrapment was examined using SEM, and the role of a surfactant (TWEEN-20) in minimizing non-specific adsorption of the microorganism on the retentate side of the membrane was investigated.

Membrane Imprint Assay

Filtration of *L. monocytogenes* in HDM broth was first carried out over nylon, mixed cellulose ester, and PVDF membrane that had 0.45 μm pore size cut-offs, and a polycarbonate membrane with 0.4 μm pore size cut-off. Volumes of 1, 5, 10, 25, and 50 mL respectively, of HDM broth (containing 700 cfu *L. monocytogenes* per ml) were filtered using the syringe to push the fluid through the membrane. This membrane imprint assay confirmed that the cells could be concentrated on all four membranes. Next, the recovery of the cells from these membranes was examined.

Quantitation of Microorganism Concentration and Recovery Using Culture Method

The experiments were repeated using the same membranes. Instead of using the imprint assay, the membranes were placed in PBS to desorb the bacteria in microcentrifuge tubes, and the supernatant was cultured as described in the Materials and Methods. This gave colony counts from which the ratio of cell count in the retentate to the initial cell count in the HDM broth was determined. Analysis of these data with the theoretical maximum showed that over half of the cells were unaccounted for.

Mechanisms of Cell Retention by Membranes

Three possibilities for lack of full recovery of concentrated cells were considered: (i) passage of cells through the membranes with the filtrate or permeate; (ii) loss of viability of cells; and/or (iii) non-specific adsorption of cells onto the membrane. Plating out of the filtrates eliminated possibility (i) since number of cells in the filtrates were statistically insignificant after 24 hours of culture on MOX. Plating out of the starting material also showed cells retain viability during the two hour time period over which membrane filtration was done, hence suggesting possibility (ii) was unlikely as the only explanation. Fluorescent microscopy images suggested that possibility (iii) offered an explanation, as well, because cells remain on the membrane'ss surface after washing with buffer. The number of cells remaining on the membrane was greatly reduced after the membrane was submersed in 0.5 ml of PBS with 1% TWEEN-20 (i.e., PBST).

PVDF, nylon and cellulose are known as depth filters, whose paths are tortuous. Pore structure is the result of stacking layers of porous materials. By design, the inter-connected pore structures of these types of membranes retain cells by entrapment, thus ensuring effective removal of microbes, and a sterile permeate. However, entrapment of a microbial pathogen such as *L. monocytogenes* is not desirable since these may be difficult to recover and analyze. As assay designed to interrogate a microbial sample for presence of pathogens requires that as many cells as possible be recovered for subsequent processing. The polycarbonate membrane filter is a screen filter that has a more uniform pore size distribution and straight pathways through the membrane. This type of membrane is less likely to entrap cells larger than the average pore size. Recovery is further hindered when cells are adsorbed due to weak hydrophobic, van der Waals force and/or physical interaction with the membranes' surface. Desorption of all cells from the polycarbonate membrane using buffer alone was found to be insufficient. Addition of surfactant (TWEEN-20) to the buffer promoted desorption perhaps by reducing surface tension of the membrane. Effect of TWEEN-20 (Surfactant)

TWEEN-20, a non-ionic detergent known to eliminate non-specific binding for immunoassays, significantly enhanced *L. monocytogenes* recovery by a factor of between 5 to 20 when the initial solution had counts of 700 cells (as cfu)/mL in HDM broth. After filtration, the highest recovery rate attained was 86%.

Previous studies showed that 1% surfactant (TWEEN-80, polyoxyethylene sorbitan monooleate) in cheese had little effect on growth of *L. monocytogenes* after the detergent was incubated with the bacteria for 10 minutes (Besse and Lafarge, 2001). However, *L. monocytogenes* growth in 1% TWEEN-20 (PBST) may give inconsistent results because the PBS with 1% TWEEN-20 (PBST) has no carbon source. Nonetheless, the viable cell count is stable over 30 minutes after which the cells die gradually over a several hour period. The cells, once concentrated, should therefore be recovered and processed within 30 mm.

Comparison of Polycarbonate and Mixed Cellulose Membranes

Nucleopore polycarbonate and MicronSep mixed cellulose membranes were chosen to further test their effectiveness for recovery of cells in PBST. The polycarbonate membrane gave 70% recovery of *L. monocytogenes*, with an overall concentration factor of 72 while MicronSep mixed cellulose membrane gave 58 fold concentration starting from around 35000 microorganisms in 50 mL (or 700 cells/mL) which were collected in 500 μL retentate. It should be noted that all bacteria were retained, as there were none detected in the filtrates. However, plating out gave only a count of the living organisms, and it was on this basis that recovery was reported. This is a key parameter since living bacteria (not dead ones) are pathogenic in this case.

Effect of Pore Sizes for Polycarbonate and Mixed Cellulose Membranes

The recovery of cells was improved from less than 10% (membranes suspended in PBS) to higher than 70% (in PBS with 1% TWEEN-20). However, a higher recovery was still the goal. Since micrographs of the membrane surfaces showed entrapment of microbes, membranes with 0.2 micron nominal pores were tested. Under the same experimental conditions, Nucleopore polycarbonate (0.2 □m pores) and MicronSep mixed cellulose (0.22 μm) were more efficient in capturing microorganisms and concentrating them than the 0.4 or 0.45 μm membranes. The concentration factor was 95 × for Nucleopore polycarbonate and 60 × for MicronSep.

The concentration factor, which gives the ratio of the total number of living cells in the retentate to the total living cells in the starting solution, increases with increasing volume of solution that is filtered for both the 0.2 μm pore cut-off polycarbonate membrane and the 0.22 μm mixed cellulose membrane.

Samples containing 15 cells/ml of HDM broth were tested to mimic a sample that might be derived from hotdogs. Different volumes were filtered through the same membrane apparatus. A linear relationship between filtered volumes and recovered cells with 63 to 80% recovery resulted.

Example 2

This example describes selective capture of one living microorganism from another by an antibody immobilized on a lysine-modified polycarbonate membrane. Capture of a relatively large microbial entity (*L. monocytogenes* at 1 micron) by a 20-fold smaller ligand (the antibody) occurs with high efficiency, when a spacer (poly-L-lysine) reacted to the membrane's surface is derivatized with an antibody (P66) specific to *Listeria*. This example further demonstragtes that isolation of the food pathogen *L. monocytogenes* from *E. coli* in less than 2 hours is possible.

Materials and Methods

The method of Suye et al. (1998) coated the polycarbonate surface with poly-L-lysine (Sigma, Cat. #P6516). The amino group at one end of the poly-L-lysine, a 14.6 kD hydrophilic spacer consisting of approximately 113 lysine monomers, activates the carbonate group of polycarbonate membrane matrix. The amino group at the other end of the poly-L-lysine is activated by addition of glutaraldehyde. The glutaraldehyde also reacts with unprotected sites on the membrane's surface. The protein links to glutaraldehyde cross-linked to the membrane matrix or to the poly-L-lysine. Soltys and Etzel (2000) had previously shown that another hydrophilic spacer, polyethylene glycol PEG, enhances the activity, binding capacity and stability of sensing layers.

Polycarbonate membrane from Osmonics (0.2 μm, 25 mm dia., Cat #K02SH02500) was cut into 1.23 $cm^2$ quarters for batch incubation. Each piece of membranes was placed into a 24-well plate containing the 0.5 ml of poly-L-lysine solution (2 mg/ml in 50 mM sodium carbonate) in 24-well plate and incubated at room temperature for 24 hours. The membranes were then rinsed and washed with deionized water. Glutaraldehyde (v/v 1%, 0.5 ml in PBS buffer, which is 10 mM with 0.2 M NaCl, pH 7.4) was added into each well and incubated for 2 hours at room temperature followed by washing and rinsing with deionized $H_2O$ and finally PBS buffer. Bovine serum albumin (BSA, Sigma, Cat #A2153), antibody P66, or FITC-labeled forms of these proteins were then added.

The polyclonal antibody (P66) against *L. monocytogenes* was generated in rabbits at a concentration of 0.6 mg/ml (Bhunia, 1997). The antibody was immobilized by adding 0.5 ml of 1:50 dilution 0.6 mg/ml P66 or FITC-P66 antibody to the poly-L-lysine/glutaraldehyde treated membranes, incubating overnight, rinsing with PBS, and then finally incubating with BSA (0.5 ml at 1 mg/ml) for 40 min (P66 membrane). BSA served as a blocking agent that prevented non-specific binding (Huang et al, 2003 (a,b)). BSA or FITC-BSA was immobilized by adding 0.5 ml of 1 mg/ml BSA to the poly-L-lysine/glutaraldehyde treated membranes and incubating overnight in the presence of air (BSA membrane). The FITC protein emited fluorescence that is readily detected using a fluorescence microscope. Antibody that was not cross-linked was washed off during buffer rinsing. A poly-L-lysine/glutaraldehyde treated membrane covalently bound P66 antibody or BSA which was retained strongly while lack of poly-L-lysine and glutaraldehyde resulted in unstable binding. FITC-P66 and FITC-BSA treated membranes glowed intensely, showing that labeled BSA or P66 was immobilized.

Binding of bacteria in batch incubation method was tested using *L. monocytogenes* V7 and *E. coli* ATCC 52739 at an undiluted concentration of about $7.3 \times 10^8$ cells/ml. The cells were labeled with FITC as following. A 2 mg of fluorescein isothiocyanate (FITC, Sigma, Cat#F4274) was dissolved in 1 ml of carbonate-bicarbonate buffer (pH 9.6). One milliliter of freshly cultured bacteria was centrifuged at 10000× rpm for 5 minutes. The supernatant was decanted and 1 ml of FITC solution was added and incubated with the bacteria for 40 minutes. The cells were then rinsed with carbonate-bicarbonate buffer three times (Bhunia et al., 1994). A volume of 0.5 ml of FITC-bacteria (~$3.7 \times 10^8$ cells) was added into wells of a 24-well plate containing P66 or BSA membranes and incubated for 40 minutes. Unbound bacteria were rinsed 3 times by pipetting 1 ml of PBS solution into each well and then removing the fluid.

For flow experiments, 25 mm, P66 derivatized, whole membranes were placed into a syringe holder (Millipore, Cat #SX00002500) and connected to a 60 ml syringe (BD, Cat #309663), which was placed into a syringe pump (Havard apparatus, PHD2000). A volume of 50 ml of bacteria in PBS buffer (pH 7.4) (~$3.7 \times 10^9$ cells) was pushed through the membrane at 5 ml/min, and the membrane was removed and placed in 3 ml of PBS for 30 minutes in order to wash off unattached cells. The washed membrane was then examined using fluorescence or scanning electron microscopy (SEM).

Results

Fluorescent microscopy showed that *L. monocytogenes* attached non-specifically to poly-L-lysine/glutaraldehyde membranes and was not removed by extensive washing with PBS buffer. BSA covalently bound to the membrane using poly-L-lysine/glutaraldehyde blocked *L. monocytogenes* adsorption. When *L. monocytogenes* was contacted with P66 membrane, it bound while *E. coli* did not.

The flow-through experiment showed *L. monocytogenes* exhibits higher retention on P66 membrane than *E. coli* ($P<0.001$). This was confirmed by the corresponding SEM's on P66 membranes contacted with either *L. monocytogenes* or *E. coli* at a concentration of $7.3 \times 10^7$ cells/mL. The scanning electron micrographs also show that the coating that was have placed on the membrane preserves cell viability. The SEM's of the *L. monocytogenes* and *E. coli* both showed cells that were dividing although it was not known if the cells adsorbed in this state or if division occurred after adsorption. The fraction of cells captured was calculated based on the micrographs. *L. monocytogenes* formed a monolayer on P66 membrane. The cell density on the membrane's surface (based on 3 different SEM images) corresponded to 10 to 20% recovery of cells from the fluid phase. In comparison, *E. coli* had a much lower retention rate (0.8 to 1.8%) and was not distributed uniformly on the surface of the P66 membrane.

The use of the antibody-derivatized membrane enabled rapid concentration of microorganisms with selective capture of one organism from another. The specific approach described in this example demonstrates how a known and easy-to-use hydrophilic spacer could be applied to a polycarbonate membrane to enable direct and productive binding of the antibody to a microbial cell that is about 20× larger than the antibody. Steric hindrance was minimized, and a uniform coating of the target species, *L. monocytogenes* was obtained on the membrane. The capture and retention of *L. monocytogenes* over *E. coli* dominated, with the fluorescent signal for the *L. monocytogenes* being much stronger than that of *E. coli*. The membranes to which antibodies were attached via a poly-L-lysine linker combined rapid cell concentration by microfiltration with selective retention of a pathogenic organism over a non-pathogenic one.

Example 3

This Example demonstrates that rapid sample processing and concentration of microbial cells from various food products, including vegetables, is feasible using a carefully selected combination of filtration, membrane separations, and bioprocessing reagents. Such a sample preparation process could be completed in 30 minutes, drastically reducing sample prep time when compared to the conventional methods of selective enrichment, which can take up to 3-7 days.

This example also describes various procedures that can be used to optimize sample preparation so that the recovery kit described herein can be used to concentrate and recover cells from the material at hand.

The Cell Recovery Kit

One experimental setup used frequently in this example is referred to as the cell concentration and recovery kit ("CCR KiT"). The CCR KiT consisted of a 140 mL sterile syringe with luer lock outlet. The sample, including bacteria, was loaded into the syringe and the plunger replaced. Two filter holders were attached in series to the outlet of the syringe. The first filter holder was 47 mm in diameter and housed a Whatman 42 cellulose filter disk with nominal pore size of 2.5 µm. This served as a prefilter for the Nucleopore track etch 0.4 µm pore size, 25 mm diameter membrane, which was housed in the second filter holder.

The membranes were pretreated with preparation buffer before the filtration. The bacteria could not pass through the second membrane, due to size restrictions. These conditions were optimized for high cell concentration and recovery. Once the entire sample has been pushed out of the syringe and through the filtration device, a series of steps were performed to recover the cells from the membrane inside the 25 mm filter holder.

After the filtration, the 25 mm filter holder was removed and the outlet of the holder was plugged with the blue cap from a sterile 3 mL syringe. 1 mL of recovery buffer was drawn into the sterile syringe, and it was connected to the luer lock fitting at the inlet of the 25 mm filter holder, with the membrane and bacteria still inside. The recovery buffer was slowly injected into the filter holder. While holding the blue cap tight and keeping the syringe in place in the inlet of the filter holder, the entire apparatus was vortex mixed for 2 min to physically detach cells which were associated to the membrane. After 2 min, the filter holder was inverted, and the liquid drawn back out into the syringe. This method allowed the user to maintain sterile conditions and to achieve maximum recovery of bacteria from the 25 mm filter holder.

Procedures for Growth, Handling and Enumeration of Bacterial Strains

GFP *Escherichia coli*

Much of the optimization described in this example was done using GFP *E. coli* as a surrogate organism for *L. monocytogenes*. *E. coli* was transformed with the plasmid *E. coli* BL21 (DE3) Star (Invitrogen, San Diego, Calif.) which yielded green fluorescent protein (GFP) expressing *E. coli* which were resistant to Ampicillin.

It was understood that the sizes and morphologies of *E. coli* and *L. monocytogenes* may differ significantly, (1×2 µm for *E. coli*, vs. 0.5×1 µm for *L. mono*.) however GFP *E. coli* was much more conducive to development of new devices and equipment. The fact that the GFP *E. coli* expressed a green fluorescent protein greatly facilitated the process of tracking and enumerating the cells through use of fluorescence microscopy. Also, the GFP *E. coli* were resistant to Ampicillin, which allowed for ease of plating out without contamination, since most potential contaminants would not be resistant to Ampicillin. *L. monocytogenes* was used to validate devices which were developed through use of GFP *E. coli*.

Luria-Bertani+Ampicillin (LBA) media was used to grow, plate out and enumerate GFP *E. coli*. LBA broth was prepared by adding 5 g NaCl, 0.5 g glucose, 2.5 g yeast extract, and 5 g tryptone to 500 mL of DI $H_2O$. This was mixed, Autoclaved at 121° C. for 20 min, and then before use 5 uL of 50 mg/mL Ampicillin solution is added to 5 mL of broth, to bring the final concentration of Ampicillin to 50 µg/mL. This was sufficient to select for AmpR GFP *E. coli* in the growth media.

LBA plates were prepared by adding 5 g NaCl, 0.5 g glucose, 2.5 g yeast extract, 5 g tryptone, and 7.5 g agar to 500 mL of DI $H_2O$. This mixture was then Autoclaved and allowed to cool to approximately 40° C., at which time Ampicillin was added to bring the concentration of Ampicillin in the media to 50 µg/mL.

In order to inoculate the samples, the GEP *E. coil* diluted from the starting culture into PBS buffer were added to the food sample, or in the case of cells in buffer, they were diluted appropriately in PBS buffer alone. For massaged hotdog, the bacteria were added to the wash buffer and then the hotdog was massaged for 30 minutes, loosening surface particles and producing a clear broth of bacteria and hotdog surface material, which was then subject to subsequent processing. For stomached hotdog, the hotdog was first processed in the STOMACHER lab blender, then passed through the filtrabag to remove large particulates, and finally the diluted bacteria were added to the liquid sample. The sample was stirred for 1 minute, and then the liquid was subject to processing. In order to determine the starting concentration, the inoculated sample was plated out on selective media. This method was used in order to obtain information on the efficiency of cell concentration and recovery from a prepared sample. While this inoculation method did not provide information about the efficiency of sample preparation, it eliminated from the counts the variation inherently involved in the sample preparation.

*L. monocytogenes* and *L. innocua*

*L. monocytogenes* is a class II biohazard organism. *L. monocytogenes* is Gram positive, rod shaped, measuring approximately 1×0.5 µm, and has a net negative charge at pH 7.

The *L. monocytogenes* was grown on modified Oxford agar (MOX), which is a slight modification of the *Listeria* selective agar Oxford formulation. To make MOX agar, combine 39 g Columbia blood agar base, 2 g agar, 1 g esculin, 0.5 g ferric ammonium citrate, 15 g lithium chloride, and 1 mL of a 1% colistin solution (1 g colistin, methane sulfonate in 100 mL potassium phosphate buffer, 0.1M, pH 6.0), with 1L DI $H_2O$. Autoclave this mixture at 121° C. for 10 min, allow to cool down to 46° C. and add 2 mL of a 1% moxalactam solution (1 g moxalactam, ammonium or sodium salt, in 100 mL potassium phosphate buffer, 0.1M, pH 6.0). Mix well and pour plates.

When the *L. monocytogenes* grow on this agar, they turn the plate black, due to their ability to hydrolyze the esculin in the media to form esculetin, which reacts with the Fe in the media to form a black product. The esculin-esculetin test is a common biochemical test in bacterial identification procedures. Also, the lithium chloride in MOX provides selective pressure for the highly salt tolerant *L. monocytogenes*.

An inoculum of *L. monocytogenes* was taken from the MOX plate and transferred to 5 mL of brain-heart infusion (BHI, Difco) liquid media where it was incubated overnight at 37° C. and shaking at 200 rpm. After 12-18 hr, the concentration of *L. mono* had reached approximately $10^9$ cells/mL, and appropriate dilutions were made for each experiment. *Listeria innocua* can be grown and enumerated on the same MOX agar, and will also produce the black color upon growth, however *L. innocua* is not pathogenic to humans. The same inoculation procedure as described for GFP *E. coli* was followed for *L. monocytogenes* and *L. innocua*.

Procedures for Processing Food Material

The Seward Stomacher® lab blender (Thetford, Norfolk, UK) was used to homogenize food samples. The samples were diluted 1:10 by weight with PBS buffer and placed inside a Labplas Filtrabag with 325 um mesh size (obtained from Fisher Scientific). The bag was secured inside the Stomacher, and the door closed and secured. The sample was then stomached for 2 min at 200 rpm.

For iceberg lettuce, 50 g of lettuce was placed into the stomacher Filtrabag with 250 mL PBS buffer. The bag was secured inside the Stomacher lab blender and stomached for 2 min at 230 rpm. After stomaching, the Filtrabag was used to retain particles larger than 300 μm, and the liquid sample was poured off. GFP $E.$ $coli$ were introduced to this liquid sample for further analysis and processing steps.

For mung bean sprouts, procedures analogous to those used for the lettuce were used. 50 g of mung bean sprouts were placed in the Filtrabag along with 250 mL of PBS buffer. The mixture was stomached for 2 min at 230 rpm in the Stomacher lab blender. The liquid was strained through the 300 μm mesh and poured off. GFP $E.$ $coli$ were added to the liquid sample for further processing and analysis.

An alternative method of food sample homogenization involved use of a kitchen blender. The food sample was diluted 1:10 in PBS buffer, and then blended on "stir" for 1 min. Any experiments involving bacteria required the blender jar to be sterilized either through washing with 70% ethanol, followed by sterile DI $H_2O$, or by Autoclaving the jar at 121° C. for 20 min. This method is also accepted by USDA/FSIS as a sample preparation technique.

Lettuce was also processed using the kitchen blender. After the liquid was poured through the filter bag. This sample preparation procedure, however, yielded a very dark green solution, presumably due to the high shear of the blender rupturing the chloroplasts. Since stomaching was the favored method for other sample types, organism recovery procedures with lettuce were carried out using the stomacher rather than the kitchen blender.

Buffer Compositions

Several types of buffer were used in order to make dilutions of bacterial solutions, to aid in recovery of cells from membranes, and to pre-treat the membranes in order to achieve higher recovery and block nonspecific binding of bacteria to the membrane.

PBS Buffer

PBS buffer was used in control runs involving bacteria. From the perspective of design and optimization of cell concentration and recovery devices, PBS was ideal. Bacteria of interest in PBS buffer at the desired concentration yielded a process fluid in which no particles, fats, background microflora, or other food constituents were present, yet the environment was not harmful to the bacteria of interest.

The PBS buffer was prepared by adding 8 g NaCl, 1.15 g $Na_2HPO_4$, 0.2 g KCl, and 0.2 g $KH_2PO_4$ to a volumetric flask, and then filling to 1L with DI $H_2O$. The pH of the buffer was 7.4. If the pH was higher than this, $KH_2PO_4$ was added until the pH reached 7.4. The buffer was either sterile filtered through a 0.2 μm filter or Autoclaved at 121° C. for 20 min before use.

Preparation and Recovery Buffers

For the purpose of cell concentration and recovery, it was necessary to make buffers with an added detergent in order to weaken nonspecific association of bacterial cells to the membranes; however the level of detergent was sufficiently low as not to lyse the target cells. The detergent used in this application was TWEEN-20. The preparation buffer was used to pre-treat membranes before introduction of process fluids. The preparation buffer (PBST) consisted of 8 g NaCl, 1.15 g $Na_2HPO_4$, 0.2 g KCl, and 0.2 g $KH_2PO_4$ in 1 L DI $H_2O$, at pH 7, to which 10 mL of TWEEN-20 was added to obtain a final concentration of 1% v/v TWEEN-20 in PBS buffer.

The recovery buffer was used to increase efficiency of washing cells off the membrane after filtration of the process fluid. The concentration of TWEEN-20 in the recovery buffer was lower than in the preparation buffer because this buffer comes into direct contact with the living cells, and a high concentration of detergent could lyse the cells. The recovery buffer consisted of 8 g NaCl, 1.15 g $Na_2HPO_4$, 0.2 g KCl, and 0.2 g $KH_2PO_4$ in 1 L DI $H_2O$ at pH 7, to which 0.5 mL of TWEEN-20 was added to obtain a final concentration of 0.05% v/v TWEEN-20 in PBS buffer.

CCR KiT for Concentration and Recovery of GFP $E.$ $coli$ and $Listeria$ $monocytogenes$ from PBS Buffer The CCR KiT could be reliably used to recover and concentrate GFP $E.$ $coli$ from PBS buffer. The concentration of cells in buffer used had a marked effect on the recovery rate and the concentration factor. The recovery rates (concentration factors) obtained for runs using design concentrations of 10 cells/mL, 100 cells/mL, and 1000 cells/mL were 1% (4×), 14% (46×), and 14% (48×), respectively. These concentrations are representative of low levels of pathogens. The concentration factor refers to the concentration in the retentate divided by the concentration in the feed or initial solution. This could also be called "X fold concentration."

Since 1000 cells/mL gave the highest recovery and concentration factor for GFP $E.$ $coli$, $Listeria$ $monocytogenes$ at 1000 cells/mL was run through the CCR KiT, and 9% recovery was obtained, with a 29× recovery factor. For GFP $E.$ $coli$, the recovery was higher for 100 and 1000 cells/mL, however it dropped considerably at the extremely low concentration of 10 cells/mL.

This suggested that there could be some loading level of cells inside the system, above which more cells are excluded from adsorption, association to the membrane, or other factors which cause the cells to remain in the system rather than be recovered. For example, the prefilter contained a tortuous matrix which could have contributed to this loading of cells as they were filtered through the system.

The Ability to Concentrate and Recover Organisms Varied Among the Food Materials Primarily Due to Filterability The first question which should be asked when looking at new applications of the CCR KiT is that of filterability. It was possible to achieve repeatable filtration of 100 mL of massaged hotdog, or hotdog meat broth (HD), through the CCR KiT. Average recovery and concentration factors for massaged hotdog using the CCR KiT were 15% and 58×, respectively for GFP $E.$ $coli$. For $Listeria$ $innocua$, the recovery and concentration were 74% and 247×, and for $Listeria$ $monocytogenes$, they were 59% and 198×. These results indicate that the $Listeria$ could be recovered more efficiently than the $E.$ $coli$. This may be due to the size differences, or to the differences in interaction of the cells with the polycarbonate membrane. $E.$ $coli$ is gram negative, and $Listeria$ are gram positive, thus their abilities to interact with the cellulose depth filter and the polycarbonate membrane may be quite different. Regardless of the recovery rates and concentration factors achieved with different bacteria, this application demonstrates the utility of the CCR KiT for cell concentration and recovery when the sample is filterable.

Once the CCR KiT had been optimized using the massaged hotdog samples, the same strategy was applied to processing whole milk (not stomached or homogenized after purchase), and hotdog, mung bean sprout, and lettuce samples which were homogenized in a kitchen blender, or stomached using the Stomacher machine. Filterability challenges were encountered, however, when the CCR KiT was used to process stomached or homogenized hotdog and vegetable samples, as well as milk.

The stomached and blended hotdog samples displayed very different filterability characteristics than did the massaged hotdog samples. Since the CCR KiT was designed to accommodate a 100 mL liquid sample from massaged hotdogs, successful filtration was defined as passing 100 mL of the stomached hotdog sample through the membranes. Massaging of hotdogs is a standardized procedure developed at the USDA-ARS-ERRC.

A Filtrabag in the Stomacher was first examined in order to increase filterability by removing large particles, and to pour the liquid through the filtrabag when the kitchen blender was used. The Filtrabag is a commercially available Stomacher accessory, and has a 300 μm pore size mesh in the center which separates the Stomacher bag into two chambers, allowing the liquid to be poured off while retaining large particulates. Using the original configuration of the CCR KiT, less than 6 mL of either homogenized or stomached samples could be filtered, and at a set flow rate of 5 mL/min, the syringe pump stalled in less than 7 minutes due to excessive back pressure (>22 psi).

Several modifications were made to the types and diameters of filters in the CCR in attempts to increase filterability, however none enabled filtration of 100 mL of stomached or homogenized hotdog.

Preliminary feasibility studies were performed to investigate the applicability of the CCR KiT to whole milk. The criterion for success of filterability of milk was set at 100 mL through the CCR KiT, the same as for stomached or homogenized hotdog. When filtration of whole milk was attempted with the original setup of the CCR KiT, it was not possible to filter 100 mL.

The following modifications were made to the process, which enabled filtration of 100 mL of whole milk in 20 minutes at a set flow rate of 5 mL/min: (1) the whole milk was diluted 1:2 with PBS, and the 25 mm filter holder was replaced with a 47 mm filter holder which housed the 0.4 μm PC membrane, and (2) the whole milk (not diluted) was run through the setup described in (1). This showed that by increasing the diameter of the PC membrane from 25 mm to 47 mm, it was possible to filter 100 mL of whole milk through the CCR KiT.

Since vegetables contain far less fats and lipids than do hotdogs, it was initially assumed that they would be much easier to filter through the CCR KiT. This was not the case. The first experiment with mung bean sprouts involved stomaching the bean spouts in 0.05% PBST for 2 min at 230 rpm in the Filtrabag. The resulting liquid appeared quite clear, however it was not possible to filter 100 mL of this liquid through the original configuration of the CCR KiT (47 mm Whatman42+25 mm 0.4μ PC membrane).

Similarly to mung bean sprouts, lettuce proved to be more difficult to filter than expected. Both stomaching and blending were used to prepare lettuce samples for filtration through the CCR KiT. With hotdogs, the samples looked the same whether prepared by blending or stomaching, however this was not the case with lettuce. Liquid resulting from stomaching lettuce is pale brown to yellow, whereas the liquid resulting from blending the lettuce is bright green. The liquids derived from stomached lettuce and poured off the Filtrabag could not be filtered through the original CCR KiT in the amount of 100 mL. In three trials, no more than 20 mL could be filtered, and the syringe pump stalled in less than 10 min, at a set flow rate of 5 mL/min.

Addressing Filterability Challenges

In order to optimize recovery of organisms from the food material, a number of additional processing steps were evaluated.

Filter Aid

Filter aid, or diatomaceous earth, was used in order to increase the filterability of the stomached hotdog samples. Filter aid is an extremely porous material which has the capacity to adsorb and physically retain components of the sample which may be clogging the membranes, thus improving the filterability of the sample. When added to the liquid to be filtered and loaded into the syringe, the filter aid forms a cake which effectively acts as an additional pre-filtration step. Since this pre-filtration is contained inside the syringe, it does not increase the need for handling the sample, thus the potential for contamination remains low.

In order to evaluate the merits of this processing step, experiments were performed to test for filterability of the stomached hotdog plus filter aid, as well as to determine the cell recovery for this pre-filtration process.

First, the filterability of the stomached hotdog plus filter aid was tested. The stomached hotdog liquid was poured off from the Filtrabag and the filter aid was mixed directly with the hotdog liquid. Then the mixture was loaded into the 140 mL syringe of the CCR KiT. In order to keep the filter aid from forming a plug inside the outlet of the syringe and clogging the system, a polystyrene disk, subsequently referred to as a frit, with pore size 100 μm was sanded down to the same diameter as the syringe, and loaded into the bottom of the syringe in order to give the filter aid a level platform upon which to form the cake.

Before testing this modification of the CCR KiT with bacteria, the percentage by weight of filter aid that should be added to the stomached hotdog liquid in order to allow filterability without using excessive filter aid was optimized. While 2% filter aid showed some difficultly in filtration of 100 mL of stomached hotdog, in that it was able to filter only 2 out of 3 times, 5% filter aid allowed filtration of 100 mL, 3 times without difficulty. Therefore, 5% by weight filter aid was chosen for continuation of filter aid work.

Addition of 5% filter aid enables filtration of stomached hotdog material through the CCR KiT. It was shown that approximately 85% of GFP *E. coli* loaded into the syringe are retained in the filter cake. Although this is not favorable if the desired result is to recover the cells from the 25 mm 0.4 μm PC membrane, because the cells remain in viable form while trapped within the filter cake, 85% of the cells have been effectively concentrated into a volume which is only 17% that of the original.

Vacuum Filtration and Centrifugation Pre-processing for Filtration of Stomached Hotdog through CCR KiT Another method which allowed for filtration of 100 mL of stomached hotdog liquid through the CCR KiT involved a series of vacuum filtration and centrifugation pre-processing steps. Through experimentation with several combinations of these steps using filter paper of many different pore sizes and materials, a process which yielded consistently filterable liquid was determined. The process somaching stomaching, use of the Filtrabag, vacuum filtration over Whatman 113 and Whatman 6 filter papers, centrifugation, and resuspension of the pellet. More particularly, 50 g of hotdog was stomached in 250 ml of PBS containing 0.05% TWEEN-20. The stomached material was poured through a Filtrabag and liquid collected. This collected liquid was Vacuum filtered though Whatman 113 paper. The filtrate was collected and Vacuum filtered through Whatman 6 paper. This filtrate was concentrated in a centrifuge for 5 min at 10,000×g. The supernatant was removed and pellet resuspended in 250 ml PBS containing 0.05% TWEEN-20. The resuspended pellet was filterable through the CCR KiT using a 47 mm 2.5 µm Whatman 42+47 mm 0.4 µp PC membrane configuration.

Next cell recovery using this process was determined. This was done by inoculating the hotdog liquid which was poured off from the Filtrabag with GFP *E. coli* at a design concentration of 1000 cfu/mL, plating it out, then plating out after each subsequent process step. 43% of the cells originally present in the system were present in the resuspended pellet, which can be introduced directly to the CCR KiT. The vacuum filtration through Whatman 113 had a recovery of 82%, which was slightly better than the Whatman 6, with 73% recovery. Of those cells present in the Whatman 6 filtrate, 75% of the cells were retained in the pellet after centrifugation at 10,000×g for 5 min. Knowledge of the recovery for each individual step is useful for optimizing pre-processing procedures for various other samples.

Because it was not possible to filter 100 mL of the stomached mung bean material directly from the Filtrabag through the CCR KiT, the vacuum filtration and centrifugation approach developed for the hot dog was implemented with this sample. Using the same vacuum filtration and centrifugation approach as described above for the stomached hotdog, greater than 100 mL of liquid sample derived from mung bean spouts could be consistently filtered through the CCR KiT.

Vacuum Filtration and Centrifugation Pre-processing for Filtration of Stomached Hotdog through Hollow Fiber A hollow fiber membrane was also used to filter pre-processed hotdog-derived liquid samples. A 0.45 µm hollow fiber was used to perform tangential filtration of said liquid, using a 47 mm, 2.5µ Whatman 42 filter paper as a pre-filter. Analogous to the CCR KiT, a 47 mm 2.5 µm Whatman 42 pre-filter was placed in line before the final cell recovery step, in this case the hollow fiber rather than the PC membrane. Essentially, the hollow fiber is being used in place of the 0.4 µm PC membrane from the CCR KiT, in order to carry out tangential rather than normal flow microfiltration for recovery of bacteria from food derived samples. The hollow fiber was capable of filtering 100 mL of this liquid in 15 min.

Example 4

In certain applications of the invention, the presence and viability of recovered organisms is determined using a biochip. In these applications, it is advantageous to reduce the volume of the organism-containing sample and to avoid the presence of compounds that are incompatible with the biochip. In this example, a straw concentration device was used to concentrate relatively clean solutions of GFP *E. Coli* in PBS buffer to drastically reduce the volume of the sample so that it could be introduced to a biochip.

Figure 2:
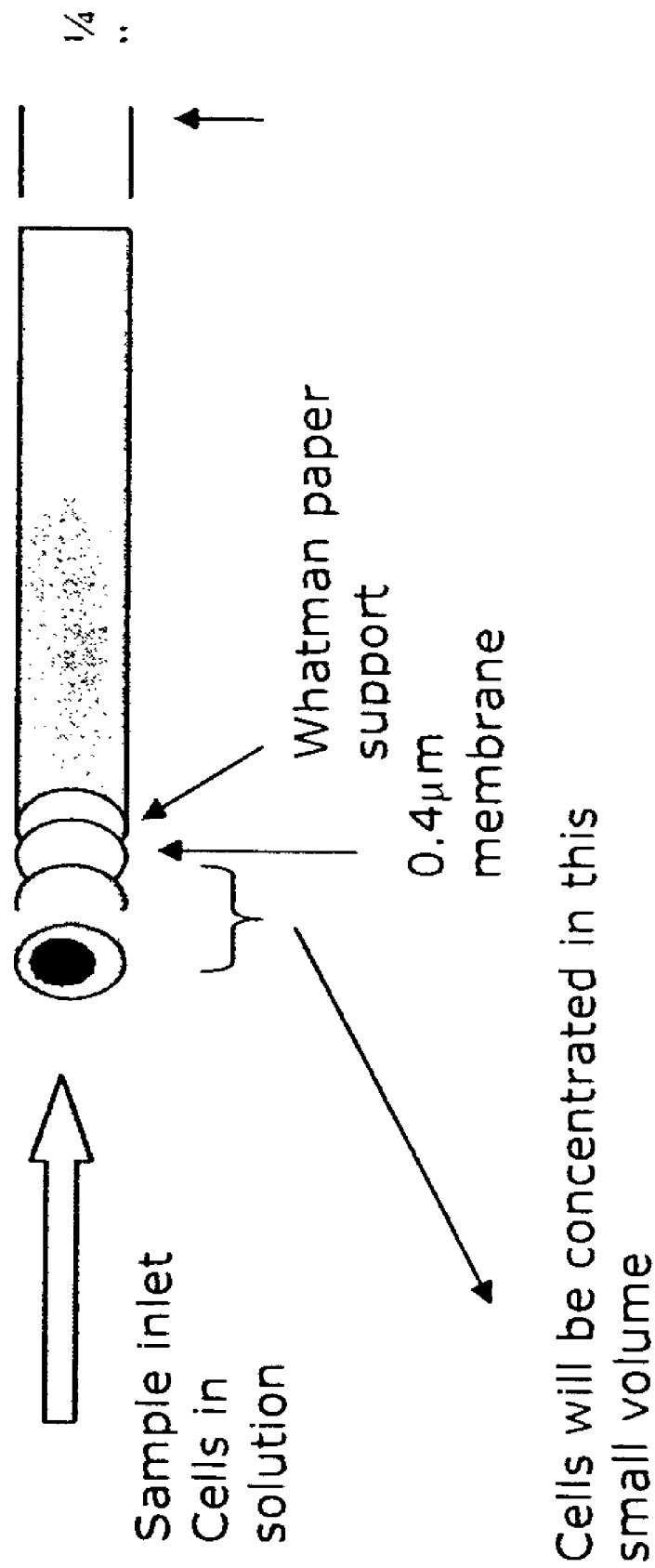
FIG. 2 is a schematic of straw concentration device.
Figure 3:
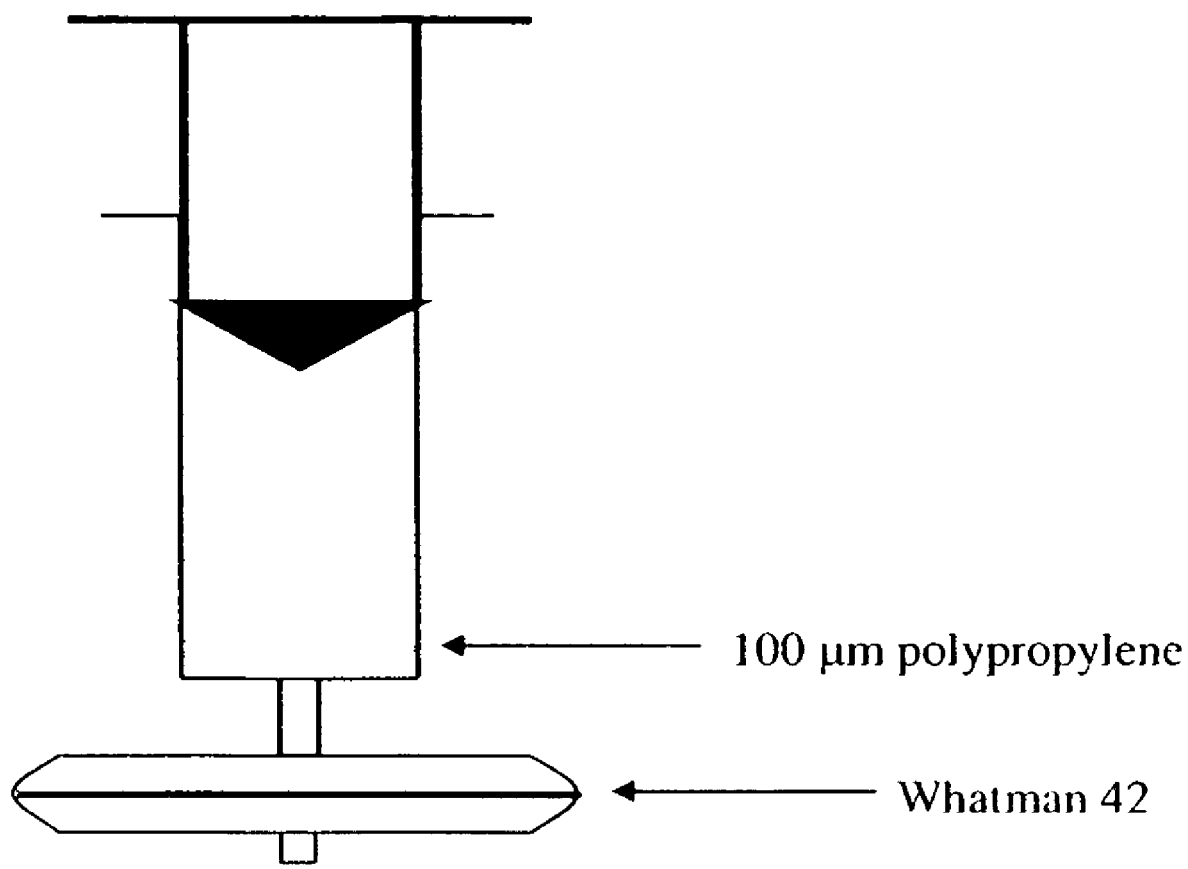
FIG. 3 illustrates a diatomaceous earth filtration setup packed with 100 μm polypropylene frit.

The straw concentration device (SCD) was made up of a ¼" outside diameter tube inside a ¼" inside diameter tube, where the inner tube has been cut and a 0.4 um membrane supported by a 2.5 um depth filter are held. See FIG. 2 for a schematic representation of this device.

After 100 mL of the solution was filtered through the membrane straw apparatus, the direction of flow was reversed and fractions of various volumes were recovered and plated out to determine the levels of concentration and recovery achieved through use of this device.

Another equivalent recovery method was also tested in which the membrane was removed. After 100 mL was filtered, the large outer tube was removed and the membrane was placed in 500 µL of PBS buffer in a 1.5 mL microcentrifuge tube and vortex mixed for 1 min. After 1 min, the membrane was removed from the first centrifuge tube and placed into a second microcentrifuge tube with 500 µL PBS. This process was repeated until 5 microcentrifuge tubes had been vortex mixed. Samples from each of these fractions were plated out to determine the concentration of cells in each fraction.

The straw concentration device, or SCD, operated on the principle of vacuum filtration and was used to concentrate solutions of GFP *E. coli* in PBS buffer from an initial cell concentration of approximately 200 cfu/mL to up to 10,000 cfu/mL. It was possible to achieve recovery of 30%, and to reduce the volume of the entire sample from 100 mL down to 50 µL, which could then be loaded onto the biochip. Using the straw concentration device described in this example, it is contemplated that if 5 mL of a relatively clean fluid was obtained from the CCR KiT, or some modification thereof, it could be concentrated to 50 µL in less than 5 minutes.

Example 5

This example demonstrates the filtration of a homogenized sample through the CCR KiT or a modified CCR KiT after first processing through a rolled stationary phase and through diatomaceous earth. The rolled stationary removes large particulates while microbes, which are fragile, are able to pass through unscathed. The use of the filter aid showed that membrane filtration on a homogenized sample can be reproducibly done. The void fraction of hydrated filter aid is greater than 90% and indicates the packed bed is very porous and suggests that bacteria may be able to be washed out of the void volume.

Rolled stationary phase (RSP) filtration involves the use of a rolled textile. The basic construction of this type of filtration apparatus is provided in U.S. Pat. No. 5,808,010 which is incorporated herein by reference in its entirety. The RSP used in this example differed from a spiral wound module by not comprising a mesh spacer between the individual fabric layers.

Briefly, bleached cotton flannel (Testfabrics, Inc.) was cut into a rectangular shape in the bias direction. Each swatch was approximately 160 cm×22 cm. In order to make a longer one, two swatches had to overlap. The fabric was laid on a dry, hard, smooth surface and wetted to dampness with deionized water. A small initial roll was begun at one end of the swatch. During the rolling process, even pressure was applied with the fingers until the bolt reaches the palm of the hand and then the fingers are placed back on the bolt and this is repeated until there is a monolithic bolt. In order to make the bolt tighter, the rolling was resumed on a dry, hard, smooth surface and rolled with an outward pressure from the fingers. Rolling is also described by Hamaker et al., 1998.

The filter holder was made using parts from 2 Swagelok 1"-½" reducing unions. The rolled stationary phase was cut to 6" and packed by hand into the housing.

The bacteria used in this example were a non-pathogenic strain of *Escherichia coli*. The competent *E. coli* cell line, BL21 Star (Invitrogen), catalog number C6010-03, were transformed with the plasmid pQBI T7-GFP (Quantum Biotechnologies) to get Green Fluorescent Protein-*E. coli*.

Phosphate Buffered Saline (PBS) buffer was used in this example. It comprised 8 g Sodium chloride, NaCl (Sigma), 1.15 g Sodium phosphate, dibasic, anhydrous, $Na_2HPO_2$ (Sigma), 0.2 g Potassium chloride, KCl (Sigma), and 0.2 g Potassium phosphate, monobasic, anhydrous, $KH_2PO_4$ (J.T. Baker). Deionized water was then used to make a 1 liter solution of PBS buffer. The pH was 7.45. A 0.05% solution of Polyoxyethylenesorbitan Monolaurate or TWEEN-20 (Sigma) in PBS buffer was used. All reagents were autoclaved after they were made.

The hotdogs used in this example were Oscar Mayer bun length hotdogs. Each hotdog was torn in eighths and placed in 250 mL of PBS. The contents were then blended for 1 minute on the stir setting of a Kitchen Art blender. The resulting homogenate was then placed in a Fisherbrand dual chamber stomacher bag (01-002-57) which has a mesh size of 300 μm. The filtrate that did not get through was squeezed through, retaining the solids on the other side. This resulting filtrate will thus be referred to as homogenized stomached hotdog (HSH) solution.

A stir bar was put in the HSH solution in order to cause turbulence at the surface of the fabric to slow the process of concentration polarization. After 2 hours, the outer layer of the fabric was cut off because of fouling and the system proceeded for another two hours. Approximately 300 mL of filtered HSH solution was collected and then processed through a modified or unmodified version of the CCR KiT. As described above, the unmodified kit contained a 47 mm holder in sequence with a 25 mm holder. The modified kits used in this example contained just one 47 mm holder or two 47 mm holders sequentially. The total filtration time for 300 mL of RSP filtered HSH solution was approximately 4 hours.

The unmodified CCR KiT comprised a 140 mL luer lock syringe (Harvard Apparatus) connected to a 47 mm and 25 mm Millipore Swinnex filter holder. The 47 mm filter holder, with 2 O-rings in it, was loaded with a Whatman 42 membrane (cut to size) while the 25 mm holder was loaded with a 25 mm 0.4 μm polycarbonate membrane. A sample was loaded into the syringe/membrane couple and placed into a Harvard PHD 2000 syringe pump. The pump convects the fluid at a 90° angle to the surface. If microorganisms are present, they will be retained on the recovery membrane (0.4 μm polycarbonate membrane).

Microorganisms are recovered by unscrewing the 25 mm holder and washing the cells off with a recovery buffer. A syringe was used to remove the liquid from the 25 mm holder and this cell solution was centrifuged and the supernatant washed off. The cells were resuspended and enumerated or introduced into a biochip.

RSP removes particulates to the point of no turbidity so the filtrate was introduced into the CCR configuration. The CCR and modified CCR KiT were tested with different membranes and membrane combinations (Table 1). Table 2 shows the results of RSP filtered HSH solution with different membrane configurations with different pore sizes. The modified CCR (47 mm) was tried first because if the prefilter clogs, then there would be no need for adding the screen filter. It was able to filter 100 mL of volume and so the CCR configuration was tried and it was unsuccessful. This suggested that the 25 mm 0.4 μm polycarbonate filter was plugging somehow with particulates smaller than the nominal pore size rating of 2.5 μm. The next step was to centrifuge the RSP filtered HSH solution to remove the particulates and filter the supernatant through the CCR. This procedure was unsuccessful which identified that the constituents in this RSP filtered HSH solution were not affected by a gravitational force. As a result of the clogging of the polycarbonate filter, a smaller prefilter (1.2 μm mixed cellulose ester) was used. The basis for its use was that particulates less than 2.5 μm and greater than 0.4 μm were impeding the processing of 100 mL of sample through the CCR and that most of these particulates were greater than 1.2 μm in size. It was unsuccessful suggesting that there were particulates smaller than 1.2 μm that were clogging the polycarbonate filter. A hydrophobic PTFE membrane was next used to see if there were hydrophobic particulates that would adsorb to the membrane surface and allow the hydrophilic constituents to pass to prevent clogging the polycarbonate filter. This was again unsuccessful. There were three different depth filters used as a prefilter and so a 0.4 μm prefilter was used. If the prefilter were to retain particles bigger than its absolute rating, then the 25 mm membrane would not be clogged which turned out to be unsuccessful.

There were then two screen filters sequentially. The pressure build up was again on the 25 mm polycarbonate membrane so there were particulates less than 0.4 μm that were clogging the filter. There were smaller particulates that were clogging the 25 mm membrane and so the increase in tortuousity with two depth filters may retain more of the smaller particulates. It worked with just the 47 mm holder but not with the 25 mm polycarbonate membrane in either of the trials. The next option was to increase the surface area of the second polycarbonate 0.4 μm membrane. The reason for doing this was that if the area is larger, more volume can be processed and Table 2 shows that two 47 mm holders sequentially with a depth filter followed by a screen filter was able to process 100 mL of RSP filtered HSH solution. In these tests, the only way for the CCR to filter 100 mL of solution was to not use the 25 mm membrane filter holder. This suggested that there is some proportionality between the volume of RSP filtered HSH solution processed and the membrane area.

TABLE 1

Membranes used and their manufacturers

| Filter Rating | Particle Retention | Material | Manufacturer |
|---|---|---|---|
| Nominal | 2.5 μm | Cotton linter cellulose | Whatman |
| Nominal | 0.1–40 μm | Glass fiber | Gelman |
| Nominal | 1.2 μm | Mixed celllose ester | Millipore |
| Nominal | 2 μm | PTFE | Pall |
| Nominal | 0.2 μm | Glass fiber | Pall |
| Absolute | 0.4 μm | Polycarbonate | Millipore |

TABLE 2

Different membrane configurations and the ability to process 100 mL of RSP filtered HSH solution through the CCR KiT and modified versions of the CCR KiT

| Filter Type | Particle Retention | Holder Diameter | Material | Results | | |
|---|---|---|---|---|---|---|
| Depth | 2.5 μm | 47 mm | Cotton linter cellulose | ✓ | | |
| Depth | 2.5 μm | 47 mm | Cotton linter cellulose | X | X | X |
| Screen | 0.4 μm | 25 mm | Polycarbonate | | | |
| Depth | 2.5 μm | 47 mm | Cotton linter cellulose | $X^c$ | | |
| Screen | 0.4 μm | 25 mm | Polycarbonate | | | |
| Depth | 1.2 μm | 47 mm | Mixed cellulose ester | X | | |
| Screen | 0.4 μm | 25 mm | Polycarbonate | | | |
| Depth | 2 μm | 47 mm | PTFE | X | X | X |
| Screen | 0.4 μm | 25 mm | Polycarbonate | | | |
| Screen | 0.4 μm | 47 mm | Polycarbonate | X | | |
| Screen | 0.4 μm | 25 mm | Polycarbonate | | | |
| Screen | 0.4 μm | 47 mm | Polycarbonate | X | | |

TABLE 2-continued

Different membrane configurations and the ability
to process 100 mL of RSP filtered HSH solution
through the CCR KiT and modified versions of the CCR KiT

| Filter Type | Particle Retention | Holder Diameter | Material | Results | | |
|---|---|---|---|---|---|---|
| Depth | 2.5 μm | 47 mm | Cotton linter cellulose | ✓ | X | ✓ |
| Screen | 0.4 μm | 47 mm | Polycarbonate | | | |
| Depth/Depth (2 in one holder) | 0.1–40 μm & 2.5 μm | 47 mm | Glass fiber/ Cotton linter | | ✓ | |
| Depth/Depth (2 in one holder) | 0.1–40 μm & 2.5 μm | 47 mm | Glass fiber/Cotton linter cellulose | X | | X |
| Screen | 0.4 μm | 25 mm | Polycarbonate | | | |
| Depth/Depth (2 in one holder) | 0.2 μm & 2.5 μm | 47 mm | Glass Fiber/ Cotton linter cellulose | X | | X |
| Screen | 0.4 μm | 25 mm | Polycarbonate | | | |

✓ = Able to filter 100 mL of sample through the CCR KiT
X = Not able to filter 100 mL of sample through the CCR KiT
Hotdog weight ≈ 50 g
C = Centrifugation at 11,400 g for 25 minutes Diatomaceous Earth Filtration of Homogenized Hotdogs Diatomaceous earth filtration was another vehicle used to facilitate processing of a homogenized meat sample because of the inability of the RSP to filter out colloidal particulates from the HSH solution. The basis for using diatomaceous earth was that each particle has a porosity within it that helps retain some of the colloidal particles. In order to be applied to the CCR, it would be appropriate to make sure that the homogenized sample would be able to be filtered through the 47 mm Whatman 42 membrane and then if bacterial cells would be able to be concentrated using a filter aid.

Different weight percentages of filter aid (J T Baker, 1939-1) in 120 mL of HSH solution were made and the resulting solution was filtered through a modified version of the CCR KiT using a Harvard PHD Infuse/Withdraw pump on the Sherwood-Monoject, 140 cc setting. The experimental setup is shown FIG. 3. Each run was made at 10 mL/min. A 100 μm polypropylene frit was used (Ace Glass, Inc.). The frits were purchased with a size of 50 mm and then trimmed to a diameter of approximately 38 mm with a belt sander.

As the weight percentage of the filter aid in HSH solution increased, the filtrate volume decreased and the amount occupied by the filter aid increased. This result was reasonable because filter aids can adsorb more than their weight in water. Filter aids are solid, incompressible materials that are added to the solids being filtered and increase the porosity of the filter cake and facilitates the passage of liquid through it (Ladisch, 2001). The filtrate volume collected decreased with increasing filter aid concentration because the filter aid may be absorbing some of the aqueous portion of the solution and trapping some of the insoluble particulates in the HSH solution. The liquid portion gets through while most of the solids are retained through the tortuous maze of the filter aid.

Next, retention of GFP-*E. coli* in the filter aid after filtration through the 47 mm filter holder that was loaded with a Whatman 42 membrane was detrmined. Using conservation of mass, of the cells that were plated from the 2% filter aid in HSH solution, 90.4% are retained in the filter aid after filtration. This means that 9.6% of the microbes can be recovered and that 90.4% of the cells are concentrated in approximately 7 mL of hydrated filter aid after filtration of bacterial cells in a 2% filter aid solution. So a concentration factor of 17 is obtained.

REFERENCES

Belter, P. A., E. L. Cussler, and W-S. Hu, Bioseparations: Downstream Processing for Biotechnology, Wiley-Interscience, J. Wiley and Sons, NY, 1-9, 15-18, 22-30, 238-239, 242-247 (1988).

Besse and Lafarge, Development of a membrane filtration method for enumeration of *Listeria monocytogenes* from soft cheese. 2001 Food Microbiol 18:669-676.

Bhunia. Antibodies to *Listeria mononcytogenes.* 1997 Crit. Rev. Microbiol. 23:77-107.

Chen, W-T., R. L. Hendrickson, C-P. Huang, D. Sherman, T. Geng, A. K. Bhunia, and M. R. Ladisch, "Mechanistic Study of Membrane Concentration and Recovery of *Listeria monocytogenes*," Biotechnol. Bioeng. 89,(3)-5 February 2005, Pages: 263-273.

Coulanges et al., Esculetin antagonizes iron-chelating agents and increases the virulence of *Listeria monocytogenes.* 1996 Res Microbiol. 147:677-685.

Deisingh, A. K., and M. Thompson, 2002, Detection of infectious and toxigenic bacteria, *Analyst,* 127: 567-581.

Difco Manual, 1998 p 364-366.

Frasier and Sperber, Rapid detection of *Listeria* in food and environmental samples by esculin hydrolysis. 1988 J. Food Prot. 51:762-765.

Gômez, Rafael; Bashir, Rashid; Bhunia, Arun K. 2002. Microscale electronic detection of bacterial metabolism. Sensors and Actuators B. 86: 198-208.

Hamaker, K., J. Liu, C. M. Ladisch, and M. R. Ladisch, 1998, Transport Properties of Rolled, Continuous Stationary Phase Columns, *Biotechnology Progress,* 14(1): 21-30.

Huang et al., Microfiber assisted fabrication of microfluidic channels using polydimethylsiloxane. 2003a AIChE Journal. 49:2984-2987.

Huang et al., Composite surface for blocking bacterial adsorption on protein biochips. 2003b Biotechnol. Bioeng. 81:618-624.

Hugo, W. B., and A. D. Russell, 1998, Pharmaceutical Microbiology $6^{th}$ edition, Blackwell Science, Inc., Malden, Mass., 23.

Keim et al., Modeling pore size distribution in cellulose rolled stationary phases. Biotechnol Prog. 2002 March-April; 18(2):317-21.

Ladisch, M. R. 2001. *Bioseparations Engineering*. New York: John Wiley & Sons. p. 36-47, 53-113.

Mead, P. S., L. Slutsker, V. Dietz, L. F. McCaig J. S. Bresee, C. Shapiro, P. M. Griffin, R. V. Tauxe, 1999, Food-Related Illness and Death in the United States. *Emerging Infectious Diseases,* 5(5): 607-625.

Palmgren et al., The Nucleopore filter method: a technique for enumeration of viable and nonviable airborne microorganisms. 1986 Am J Ind Med. 10:325-327.

Sharpe, A. N.; Jackson, A. K. 1972. Stomaching: a New Concept in Bacteriological Sample Preparation. Applied Microbiology. 24(2): 175-178.

Shaw et al., Nucleopore filters as diffusion screens: effect of barrel-shaped pore distortions. 1985 J Aerosol SCi. 16:307-313.

Stevens K. A., and L-A. Jaykus, 2004, Bacterial Separation and Concentration from Complex Sample Matrices: A Review, *Critical Reviews in Microbiology,* 30(1), 7-24.

Suye et al., Immobilization of glucose oxidase on poly-(L-lysine)-modified polycarbonate membrane. 1998 Biotechnol. Appl. Biochem. 27:245-248.

Swaminathan B., and P. Feng, 1994, Rapid Detection of Food-Borne Pathogenic Bacteria, *Annual Reviews in Microbiology*, 48: 401-426.

Based on the invention and examples disclosed herein, those skilled in the art will be able to develop other embodiments of the invention. The examples are not intended to limit the scope of the claims set out below in any way. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of rapid concentration and recovery of viable microorganisms from a sample, the method comprising:
    (a) providing a microorganism-containing sample, the sample comprising a liquid component having a first volume;
    (b) providing a hollow fiber filter comprising at least one hollow fiber strand, wherein the hollow fiber filter comprises fibers having a length between 1 cm and 25 cm;
    (c) reducing the first volume of the liquid component by applying the sample to the hollow fiber filter, wherein the volume is reduced by at least 1000 times;
    (d) back flushing the microorganisms from the hollow fiber filter to remove the microorganisms from the hollow fiber filter without vortexing and in a buffer having a second volume;
    (e) delivering the second volume and the microorganisms from the hollow fiber filter to a biochip device; and
    (f) detecting the presence of viable microorganisms using the biochip device.

2. The method of claim 1 comprising culturing the microorganisms in the biochip to detect the presence of viable microorganisms.

3. The method of claim 1 wherein detecting the viable microorganisms comprises measuring the change in impedance in the biochip device.

4. The method of claim 1 wherein the hollow fiber filter comprises fibers having an average pore size of less than 0.5 μm.

5. The method of claim 1 further comprising flowing the sample through a first filter.

6. The method of claim 5 wherein the first filter comprises an average pore size of 2 μm to 20 μm.

7. The method of claim 6, wherein the first filter comprises a rolled stationary phase filter or a membrane.

8. The method of claim 1, wherein (a) to (d) are performed in less than 60 minutes.

9. The method of claim 1, wherein (a) to (d) are performed in 30 minutes or less.

10. The method of claim 1, wherein the microorganisms are selected from the group of bacteria, fungi and protozoans.

11. The method of claim 1, further comprising treating the sample to provide the liquid component using one or more of the treatments selected from the group consisting of diluting, blending, chopping, centrifuging, filtering, enzyme treating, massaging and contacting the sample with a positively-charged or negatively-charged membrane or particles.

12. The method of claim 1 wherein the hollow fiber filter comprises fibers comprising polysulfone.

13. The method of claim 1, further comprising treating the hollow fiber filter with a blocking solution prior to reducing the volume of the liquid component.

14. The method of claim 13, wherein the blocking solution comprises a concentration of polyoxyethylene sorbitan monolaureate between 0.001 percent and 1.0 percent.

15. The method of claim 1, wherein the concentration and recovery of the viable micro-organisms is manually performed.

16. A method of rapid concentration and recovery of viable microorganisms from a sample, the method comprising:
    (a) providing a microorganism-containing sample, the sample comprising a liquid component;
    (b) providing a hollow fiber filter, comprising at least one hollow fiber strand, the fiber having an average pore size of less than 0.5 μm and a length of between 1 cm and 25 cm;
    (c) reducing a volume of the liquid component by flowing the sample through the hollow fiber filter, wherein the volume is reduced by at least 1000 times;
    (d) recovering viable microorganisms from the hollow fiber filter without vortexing by back flushing the microorganisms from the hollow fiber filter in a buffer having a reduced volume, the buffer being suitable for delivery to a biochip device;
    (e) flowing the buffer containing the recovered viable microorganisms into the biochip device; and
    (f) detecting the presence of the viable microorganisms using the biochip device.

17. The method of claim 16, wherein (a) to (f) are performed in less than 8 hours.

* * * * *